( 12 ) United States Patent
Wu et al.

(10) Patent No.: US 12,171,798 B2
(45) Date of Patent: Dec. 24, 2024

(54) ESSENTIAL OIL COMPOSITION AND PREPARATION METHOD THEREOF

(71) Applicant: Jiangxi University of Chinese Medicine, Nanchang (CN)

(72) Inventors: Zhenfeng Wu, Nanchang (CN); Wei He, Nanchang (CN); Di Wang, Nanchang (CN); Ming Yang, Nanchang (CN); Na Wan, Nanchang (CN)

(73) Assignee: Jiangxi University of Chinese Medicine, Nanchang (CN)

( * ) Notice: Subject to any disclaimer, the term of this patent is extended or adjusted under 35 U.S.C. 154(b) by 0 days.

(21) Appl. No.: 18/603,498

(22) Filed: Mar. 13, 2024

(65) Prior Publication Data
US 2024/0335495 A1 Oct. 10, 2024

(30) Foreign Application Priority Data

Apr. 6, 2023 (CN) .......................... 202310354588.X

(51) Int. Cl.
*A61K 36/63* (2006.01)
*A61K 9/00* (2006.01)
*A61K 47/12* (2006.01)
*A61K 47/18* (2017.01)
*A61P 31/04* (2006.01)

(52) U.S. Cl.
CPC ............ *A61K 36/63* (2013.01); *A61K 9/0014* (2013.01); *A61K 47/12* (2013.01); *A61K 47/186* (2013.01); *A61P 31/04* (2018.01)

(58) Field of Classification Search
None
See application file for complete search history.

(56) References Cited

U.S. PATENT DOCUMENTS

2022/0096402 A1\* 3/2022 Koppisch ............... A61K 31/01

FOREIGN PATENT DOCUMENTS

| CN | 101357146 A | \* | 2/2009 |
|---|---|---|---|
| CN | 106214553 A | | 12/2016 |
| CN | 107929101 B | | 4/2018 |
| CN | 108310060 A | | 7/2018 |
| CN | 109511688 A | | 3/2019 |
| CN | 111918644 A | | 11/2020 |
| CN | 114426905 A | | 5/2022 |
| WO | 2017164627 A2 | | 9/2017 |

\* cited by examiner

Primary Examiner — Susan Hoffman
(74) Attorney, Agent, or Firm — Birchwood IP

(57) ABSTRACT

Provided are an essential oil composition and a preparation method thereof. The essential oil composition includes a eutectic composition and an essential oil; the eutectic composition includes a hydrogen-bond donor and a hydrogen-bond acceptor; the hydrogen-bond donor is geranic acid or derivatives of the geranic acid; the hydrogen-bond acceptor is choline or derivatives or hydrates of the choline; a mass ratio of the hydrogen-bond donor to the hydrogen-bond acceptor is 1-10:1-10.

4 Claims, 19 Drawing Sheets

ESSENTIAL OIL COMPOSITION AND PREPARATION METHOD THEREOF

CROSS-REFERENCE TO RELATED APPLICATIONS

This application claims priority of Chinese Patent Application No. 202310354588.X, filed on Apr. 6, 2023, the entire contents of which are incorporated herein by reference.

TECHNICAL FIELD

The present disclosure belongs to the technical field of pharmaceutical preparations, and in particular to an essential oil composition and a preparation method thereof.

BACKGROUND

With the improvement of people's living standards, people increasingly favor safe and effective natural drugs. Volatile oil, namely essential oil, is an oily liquid extracted from natural plants and containing pharmaceutical active ingredients, and has high safety. With the improvement of purification technology and drug delivery means, essential oil is widely used in disease treatment. Different essential oils show certain pharmacological activities in antibacterial, anti-inflammatory, antioxidant and anticancer aspects.

In the existing transdermal drug delivery preparations, the composition with essential oil as the main component has the following disadvantages: volatile, difficult to store (essential oil gradually dissipates with the storage time), strong greasy feeling and poor skin feeling, and essential oil is easily miscible with organic solvents and difficult to reach the action site. For example, China Patent Application CN108310060A, Chinese Herbal Medicine Compound Cream for Treating Vitiligo, takes Saxifraga stolonifera Meerb. extract, *Cleistocalyx operculatus* extract, *Hibiscus syriacus* L. bark extract and *Thymus mongolicus* essential oil as effective components, and is added with octadecanol, stearic acid, liquid paraffin, vaseline, potassium hydroxide (pH regulator), glycerol and distilled water to make the cream, and the cream has a strong greasy feeling and poor skin friendliness after coating. In China Patent Application CN114426905A, Essential Oil Composite Nanoemulsion and Preparation Method Thereof, plant essential oil, emulsifier and water are made into composite nanoemulsion, but the preparation process is complicated, and the nanoemulsion is prone to demulsification during storage due to factors such as temperature, pH and contact materials. In China Patent Application CN109511688A, Woody Mosquito and Insect Repellent Compound Essential Oil and Preparation Method Thereof, China Patent Application CN106214553A, Moisturizing and Hydrating Essential Oil, China Patent Application CN107929101B, Compact Massage Essential Oil and Preparation Method Thereof, in order to improve the solubility of the essential oil in the system, the essential oil is dissolved in 50-60% ethanol, chloroform and propylene glycol respectively. These organic solvents have different degrees of irritation and damage to the skin, especially some sensitive skin and mucosa, which may not adapt to the products containing such organic solvents.

To sum up, in the prior art, essential oils are often made into ointments, emulsions, gels, nano-micelles, etc., as it is difficult to characterize, complicated in manufacturing process, and harsh in storage conditions. Those creams made of liquid paraffin and vaseline are not only greasy, but also affect the speed of transdermal penetration. In addition, liquid products dispersed in organic solvents such as ethanol, chloroform, propylene glycol, etc. are also greasy, difficult to clean, irritating to skin and mucous membranes, and even lead to skin allergies to varying degrees.

Therefore, it is urgent to develop a delivery system that may safely solubilize essential oil, improve the greasy feeling of essential oil products and simplify the preparation process of essential oil.

SUMMARY

In view of the shortcomings of the prior art, the present disclosure provides an essential oil composition (EO composition) and a preparation method thereof. According to the disclosure, the eutectic composition with a specific composition is used to promote uniform dissolution of EO in water and absorption and utilization of EO. Compared with the prior art, the greasy feeling of the EO composition is reduced, and in the EO composition, organic solvents such as ethanol, chloroform and propylene glycol are no longer used, so that the prepared EO composition is milder and less irritating, and further may be made into mucosal essential oil spray.

The present disclosure provides a EO composition, and the EO composition includes a eutectic composition and a EO; the eutectic composition includes a hydrogen-bond donor (HBD) and a hydrogen-bond acceptor (HBA); the HBD is geranic acid (Ge) or derivatives of the Ge; the HBA is choline (Ch) or derivatives or hydrates of the Ch; a mass ratio of the HBD to the HBA is 1-10:1-10.

Optionally, the HBA is 1-2 parts by mass of the Ch, and the HBD is 1-2 parts by mass of the Ge; a preparation method of the eutectic composition includes: mixing the Ch and the Ge in a reactor, heating to less than or equal to 45° C. for dissolution, stirring and carrying out reaction for more than 2 h to obtain a product, evaporating water in the product at less than or equal to 60° C., and then drying the product at less than or equal to 60° C. to obtain the Ch/Ge eutectic composition (DES).

Optionally, the HBA is derivatives or hydrates of the Ch, such as choline chloride, citicoline sodium, choline lauroyl chloride, choline hydroxide, choline bicarbonate, choline glycerophosphate, etc.

Ch is a nutritional fortifier; Ge, a plant extract, is an organic acid. The DES has the characteristics of good fluidity, and may dissolve EO and dissolve in water, promote the dissolution of EO in water without masking the original fragrance of EO and greatly reduce the greasy feeling of EO. Therefore, DES is the best essential oil delivery medium.

Optionally, a mass concentration of the EO in the EO composition is 0.1-20%.

Optionally, the EO is a volatile oil extracted from any one or more of following plants: *Syringa oblata* Lindl., *Curcuma phaeocaulis* Valeton, *Cedrus deodara*, *Fraxinus chinensis* Roxb., *Camellia sinensis*, *Eucalyptus* spp., *Liriope spicata*, *Cinnamonum cassia*, *Pelargonium hortorum* Bailey, *Salvia aerea* Levl., *Santalum album* L., *Commiphora myrrha*, *Zingiber officinale* Roscoe, *Eucalyptusrobusta Smith*, *Cananga odorata*, *Jasmimum sambac*, *Pogostemon cablin*, *Matricaria chamomilla* L., *Rosa* spp., *Citrus japonica* Thunb., *Citrus* x *limon*, *Lavandula angustifolia* Mill., *Artemisia argyi* Levl. et Vant., *Chimonanthus nitens* Oliv., *Aquilaria* spp., *Ocimum basilicum* L., *Citrus medica* 'Fingered', *Thymus mongolicus*, *Allium sativum* L., *Zanthoxylum bungeamim* Maxim., *Rosmarimis officinalis* L., *Mentha canadensis* Linnaeus, *Perilla frutescens* and *Nepeta cataria* L.

Optionally, the EO is extracted from roots, stems, leaves or fruits of the plants; an extraction method of the EO is any one or more of steam distillation, squeezing, organic solvent extraction and supercritical fluid extraction.

Optionally, the EO composition is a disinfectant for external use, a transdermal preparation or an oral preparation.

Optionally, the EO composition is a drug for treating dermatitis, atherosclerosis, fungal infection, acne, pruritus, dermatophyte, arthritis or asthma.

The present disclosure also provides a preparation method of the EO composition, including: stirring or ultrasonically mixing the eutectic composition with the EO, and diluting to a predetermined concentration without adding water or by adding water, so as to obtain the EO composition; the EO composition is a EO liquid preparation.

Optionally, in the EO liquid preparation, when the essential oil content is 1-10%, the water content is controlled at 60-70%. When the proportion of water is further increased, emulsification will occur, and oil droplets will be precipitated after standing.

Optionally, the water is any one or more of tap water, distilled water, de-ionized water and ultrapure water.

The embodiments provided by the disclosure have the following effects.

The present disclosure provides a EO composition, and in the EO composition, a eutectic composition prepared by Ch and Ge in proportion not only solubilizes EO, promotes absorption of EO and increases stability of EO, but also uniformly mixes water with EO and improves greasy feeling of EO.

The raw materials of the eutectic composition in the present disclosure are Ge and Ch, both of which have high safety. Ch is a nutritional fortifier, and Ge, a plant extract, is an organic acid. The eutectic composition may combine with EO in the form of covalent bond, and thus solubilize EO, improve skin permeability and increase drug transdermal penetration. Moreover, the eutectic composition may improve the permeability of EO (volatile oil) and the stability of EO liquid preparation, reduce volatilization, and simplify the production process of liquid preparation with EO as the main active ingredient.

According to the disclosure, the EO composition made of the eutectic composition and EO overcomes the shortcomings, like irritation, of products such as ointments, emulsions, gels, nano-micelles, creams and the like. The EO composition may be used as a disinfectant for external use, a transdermal preparation (including mucosal administration) or an oral preparation, and may also be used as a drug for treating dermatitis, atherosclerosis, fungal infection, acne, pruritus, dermatophyte, arthritis, or a drug for treating asthma by oral administration or spray for oral and nasal cavity.

DESCRIPTION OF EMBODIMENTS

Figure 1:
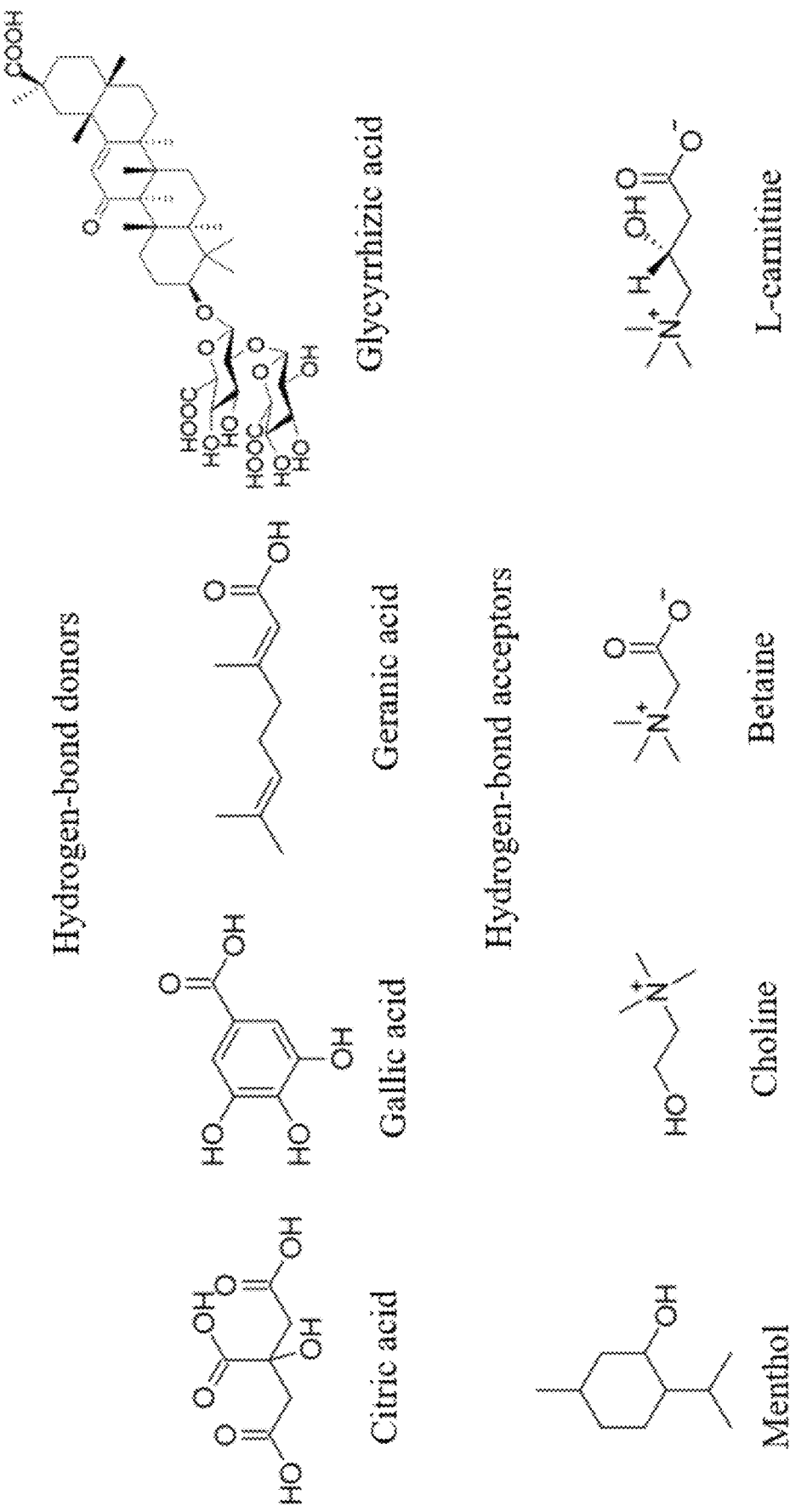
FIG. 1 shows structural formulas of some HBDss and HBAs used in the present embodiments.

In order to better explain the present disclosure and facilitate understanding, the following is a detailed description of the present disclosure through specific embodiments with the attached drawings. The raw materials used in the following embodiments and comparative examples are all from commercially available standard samples. Table 1 shows English abbreviations and substance names appearing in the drawings and embodiments in.

TABLE 1

| Essential oil | EO | Betaine | Be |
|---|---|---|---|
| De-ionized water | W | Glycyrrhizinic acid | Gly |
| Geranic acid | Ge | Choline | Ch |
| Menthol | Me | | |
| Betaine/geranic acid eutectic composition | | BG-DES | |

TABLE 1-continued

| Menthol/glycyrrhizic acid eutectic composition | GM-DES |
| Choline/geranic acid eutectic composition | DES |

FIG. 1 shows structural formulas of some HBDs and HBAs used in the present embodiments. HBDs: Ge, Gly, gallic acid (Ga), citric acid monohydrate, sorbic acid and cinnamic acid; HBAs: Be, Me, L-carnitine, tetramethylammonium hydroxide, Ch.

Embodiment 1

Figure 2:
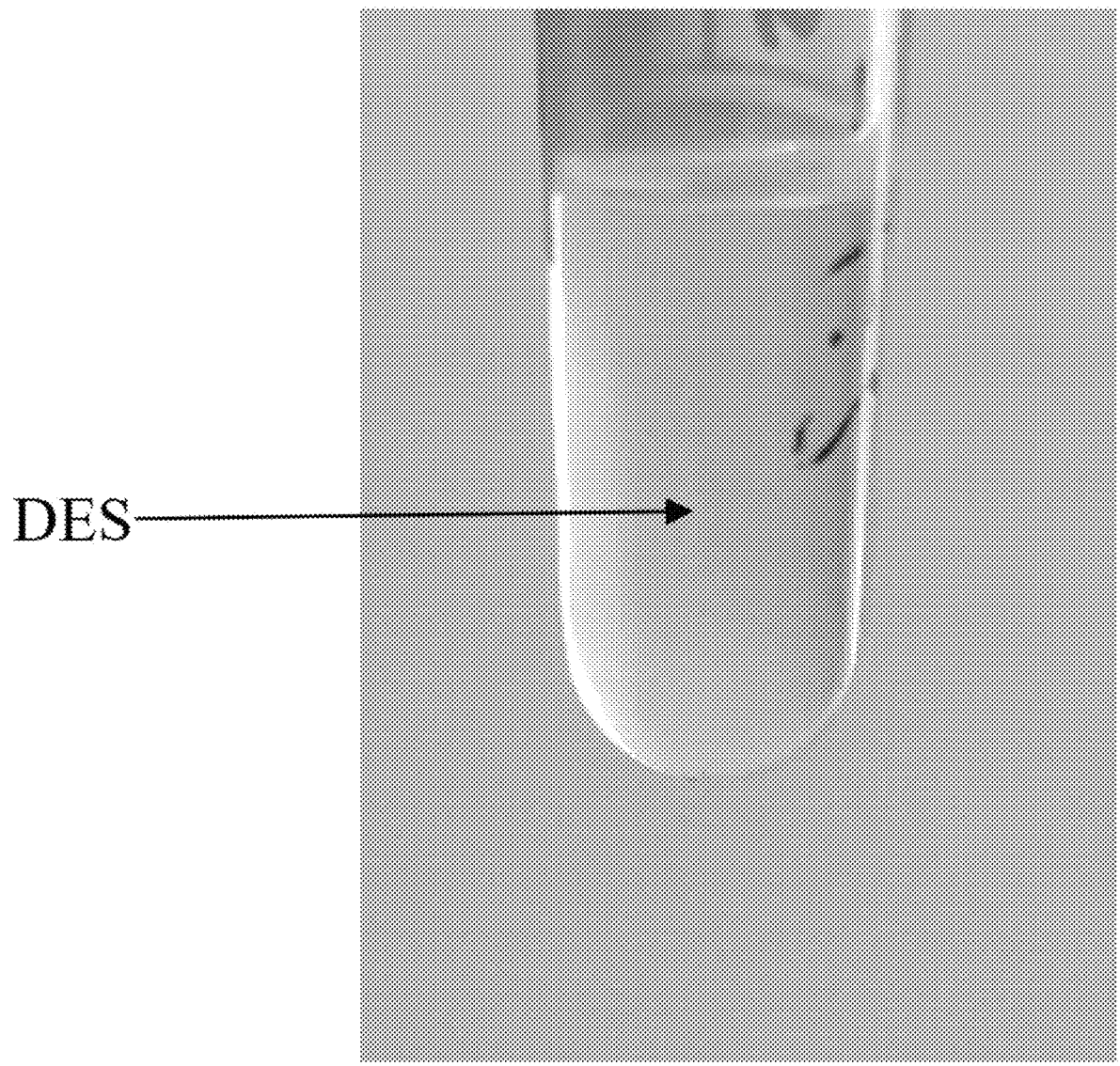
FIG. 2 shows a sample photograph of DES.

In this embodiment, Ch, as the HBA, is mixed with Ge according to the mass ratio of 1:2, 1:1 and 2:1 to prepare DES. The preparation method is as follows: heating a round-bottomed flask in a constant temperature water bath at 60° C., adjusting a rotor speed to 200-300 r/min, adding Ch and Ge into the round-bottomed flask, stirring and carrying out reaction for 12 h to obtain a product, after the reaction, performing rotary evaporation on the product in a rotary evaporator at 60° C. for 2 h to remove water (water generated by the reaction), and then drying in an oven at 60° C. to synthesize DES. The proportion of raw materials and preparation conditions are shown in Table 2. The product is a homogeneous and transparent liquid with good fluidity as shown in FIG. 2.

Comparative Example 1

In this comparative example, Me, as the HBA, is mixed with Gly according to the mass ratios of 1:10, 1:20, 1:25 and 1:30 to prepare a GM-DES. The preparation method is as follows: heating a round-bottomed flask in a constant temperature water bath at 70° C., adjusting a rotor speed to 200-300 r/min, adding the ethanol solution of Gly and the Me into the round-bottomed flask, stirring and carrying out reaction for 12 h to obtain a product, after the reaction, performing rotary evaporation on the product in a rotary evaporator at 45° C. for 20 mins to remove ethanol to obtain GM-DES. The proportion of raw materials and preparation conditions are shown in Table 2.

Comparative Example 2

In this comparative example, L-carnitine, as the HBA, is prepared into eutectic compositions with Ge, citric acid monohydrate, sorbic acid and cinnamic acid respectively. The proportion of raw materials and preparation conditions for each eutectic composition are shown in Table 2.
(1) 1 part by mass of L-carnitine and 2 parts by mass of Ge are used to prepare a L-carnitine/Ge eutectic composition. The preparation method is as follows: heating a round-bottomed flask in a constant temperature water bath at 70° C., adjusting a rotor speed to 200-300 r/min, adding L-carnitine and Ge into the round-bottomed flask and carrying out reaction for 12 h to obtain the L-carnitine/Ge eutectic composition.
(2) 1 part by mass of L-carnitine is dissolved in water to prepare an 80% aqueous solution, and then is added with 1 part by mass or 2 parts by mass of citric acid monohydrate to prepare the L-carnitine/citric acid monohydrate eutectic composition. The preparation method is as follows: heating a round-bottomed flask in a constant temperature water bath at 70° C., adjusting a rotor speed to 200-300 r/min, adding the aqueous solution of L-carnitine and the corresponding mass fraction of citric acid monohydrate into the round-bottomed flask, carrying out reaction for 12 h, and evaporating and dehydrating to obtain the L-carnitine/citric acid monohydrate eutectic composition.
(3) 1 part by mass of L-carnitine and 2 parts by mass of sorbic acid are used to prepare L-carnitine/sorbic acid eutectic composition under different conditions. One preparation method is: heating a round-bottomed flask in a constant temperature water bath at 50° C., adjusting a rotor speed to 200-300 r/min, adding L-carnitine and sorbic acid into the round-bottomed flask, and carrying out reaction for 12 h to obtain the L-carnitine/sorbic acid eutectic composition. Another one preparation method is: heating a round-bottomed flask in a constant temperature water bath at 50° C., adjusting a rotor speed to 200-300 r/min, adding the ethanol solution of L-carnitine and the sorbic acid into the round-bottomed flask, carrying out reaction for 12 h, and then removing the ethanol by rotary evaporation at 50° C. to obtain the L-carnitine/sorbic acid eutectic composition.
(4) 1 part by mass of L-carnitine and 2 parts by mass of cinnamic acid are used to prepare L-carnitine/cinnamic acid eutectic composition. The preparation method is as follows: heating a round-bottomed flask in a constant temperature water bath at 70° C., adjusting a rotor speed to 200-300 r/min, adding L-carnitine and cinnamic acid into the round-bottomed flask and carrying out reaction for 12 h to obtain the L-carnitine/cinnamic acid eutectic composition.

Comparative Example 3

In this comparative example, 1 part by mass of tetramethylammonium hydroxide (raw material is tetramethylammonium hydroxide pentahydrate), as a HBA, is mixed with 2 parts by mass or 3 parts by mass of Ge to prepare a eutectic composition. The preparation method is: heating a round-bottomed flask in a constant temperature water bath at 45° C., adjusting a rotor speed to 200-300 r/min, adding the tetramethylammonium hydroxide pentahydrate and Ge into the round-bottomed flask, stirring and carrying out reaction for 12 h, and after the reaction, carrying out rotary evaporation for 5 mins to remove water, thus obtaining the tetramethylammonium hydroxide/Ge eutectic composition. The proportion of raw materials and preparation conditions are shown in Table 2.

TABLE 2

Characteristics of eutectic compositions prepared in Embodiment 1, Comparative example 1, Comparative example 2 and Comparative example 3.

| Project | HBA | HBD | HBA solvent | HBD solvent | HBA:HBD | Homogeneous liquid | Dissolving EO | Dissolving in water |
|---|---|---|---|---|---|---|---|---|
| Comparative example 1 | Me | Gly | / | Ethanol | 1:10 | − | / | / |
| | | Gly | / | Ethanol | 1:20 | − | / | / |

TABLE 2-continued

Characteristics of eutectic compositions prepared in Embodiment 1, Comparative example 1, Comparative example 2 and Comparative example 3.

| Project | HBA | HBD | HBA solvent | HBD solvent | HBA:HBD | Homogeneous liquid | Dissolving EO | Dissolving in water |
|---|---|---|---|---|---|---|---|---|
| | | Gly | / | Ethanol | 1:25 | + | + | − |
| | | Gly | / | Ethanol | 1:30 | + | + | − |
| Comparative example 2 | L-carnitine | Ge | / | / | 1:2 | + | + | − |
| | | Citric acid monohydrate | Water | / | 1:1 | + | + | − |
| | | Citric acid monohydrate | Water | / | 1:2 | + | − | + |
| | | Sorbic acid | / | / | 1:2 | − | / | / |
| | | Sorbic acid | / | Ethanol | 1:2 | − | / | / |
| | | Cinnamic acid | / | / | 1:2 | − | / | / |
| Comparative example 3 | Tetramethylammonium hydroxide | Ge | / | / | 1:2 | + | + | + |
| | | Ge | / | / | 1:3 | + | + | + |
| Embodiment 1 | Ch | Ge | / | / | 1:2 | + | + | + |
| | | Ge | / | / | 1:1 | + | + | + |
| | | Ge | / | / | 2:1 | + | + | + |

Table 2 shows whether the HBDs are dissolved in the solvent and the mass ratio of raw materials in the preparation of eutectic composition in Embodiment 1, Comparative example 1, Comparative example 2 and Comparative example 3. Table 2 also shows the characteristics of different eutectic compositions.

The DES prepared in Embodiment 1 is a homogeneous/transparent liquid with good fluidity, may dissolve essential oil and dissolve in water without masking the original fragrance of EO, greatly reduce the greasy feeling of EO. When the DES is made into a liquid preparation with water as the main dispersion solvent, the preparation has good stability and may promote the percutaneous absorption of EO.

The GM-DES prepared in Comparative example 1 has the following characteristics: when the mass ratio of Me to Gly is 1:10 or 1:20, the obtained GM-DES is not homogeneous, and may not dissolve essential oil and not dissolve in water. When the mass ratio of Me to Gly is 1:25-30, the obtained GM-DES is homogeneous, but has obvious mint fragrance, masks the fragrance of EO when dissolving essential oil, is insoluble in water, and has a poor effect on improving the greasy feeling of EO. Moreover, the fluidity is greatly affected by temperature.

The eutectic compositions prepared in Comparative example 2 have following characteristics.

(1) L-carnitine/Ge eutectic composition is a homogeneous liquid with good fluidity, has no special odor, may dissolve essential oil, but may not dissolve in water, and has poor effect on improving the greasy feeling of EO.

(2) L-carnitine/citric acid monohydrate eutectic composition: when the mass ratio of L-carnitine to citric acid monohydrate is 1:1, the prepared eutectic composition is a homogeneous liquid, may dissolve EO but is insoluble in water, and has poor effect on improving the greasy feeling of EO; when the mass ratio of L-carnitine to citric acid monohydrate is 1:2, the prepared eutectic composition is a homogeneous liquid, may not dissolve EO, but may dissolve in water, and may not promote the dissolution of EO in water.

(3) L-carnitine/sorbic acid eutectic composition is not heterogeneous liquid with poor fluidity, and may not promote the dissolution of EO in water.

(4) L-carnitine/cinnamic acid eutectic composition is not heterogeneous liquid with poor fluidity, and may not promote the dissolution of EO in water.

The tetramethylammonium hydroxide/Ge eutectic composition prepared in Comparative example 3 has no special odor, is a homogeneous liquid with good fluidity, may dissolve essential oil and dissolve in water, may promote the dissolution of EO in water and improve the greasy feeling of EO, but is highly toxic; 50 μL tetramethylammonium hydroxide/Ge eutectic composition is smeared on the ankles of mice, and the mice die after 20 mins, so the tetramethylammonium hydroxide/Ge eutectic composition is not suitable as the delivery medium of EO.

Comparative Example 4

In this comparative example, Be, as the HBA, is mixed with Ge, Gly, Ga, citric acid monohydrate, sorbic acid and cinnamic acid respectively, so as to prepare different eutectic compositions. The proportion of raw materials and preparation conditions for each eutectic composition are shown in Table 3.

(1) Be, as the HBA, is prepared into BG-DES with Ge according to the mass ratios of 1:1, 1:2 and 1:3 respectively. The preparation method is: heating a round-bottomed flask in a constant temperature water bath at 40° C., adjusting a rotor speed to 200-300 r/min, adding Be and Ge to the round-bottomed flask, stirring and carrying out reaction for 12 h to obtain a product, after the reaction, performing rotary evaporation on the product in a rotary evaporator for 2 h to remove water (water generated by the reaction) to obtain BG-DES.

(2) Be, as the HBA, is prepared into betaine/glycyrrhizic acid eutectic composition with Gly according to the mass ratios of 2:1, 4:1 (dissolved with ethylene glycol or ethanol) and 8:1 (dissolved with ethylene glycol or ethanol) respectively. The preparation method is: heating a round-bottomed flask in a constant temperature water bath at 45° C., adjusting a rotor speed to 200-300 r/min, adding the ethanol solution of Gly or ethylene glycol solution of Gly and betaine with corresponding parts by mass into the round-bottomed flask, stirring and carrying out reaction for 12 h, and evaporating to remove ethanol (ethylene glycol is not removed), so as to synthesize the Be/glycyrrhizic acid eutectic composition.

(3) Be, as the HBA, is prepared into Be/gallic acid eutectic composition with Ga according to the mass ratio of 1:2 (dissolved by water, dissolved by ethanol and water, and dissolved by ethylene glycol, respectively). The preparation method is: heating a round-bottomed flask in a constant temperature water bath at 50° C., adjusting a rotor speed to 200-300 r/min, adding the aqueous solution of Ga, the mixed solution of Ga with ethanol and water, and the glycol solution of Ga into the round-bottomed flask, and adding the corresponding parts of Be by mass, stirring and carrying out reaction for 12 h, and evaporating to remove the solvent (glycol is not removed), so as to synthesize the Be/gallic acid eutectic composition.

(4) Be, as the HBA, is prepared into Be/citric acid monohydrate eutectic composition with citric acid monohydrate according to the mass ratio of 1:2. The preparation method is: heating a round-bottomed flask in a constant temperature water bath at 50° C., adjusting a rotor speed to 200-300 r/min, adding the aqueous solution of citric acid monohydrate and corresponding parts of Be into the round-bottomed flask, stirring and carrying out reaction for 12 h, and evaporating to remove water, so as to synthesize the Be/citric acid monohydrate eutectic composition.

(5) Be, as the HBA, is prepared into Be/sorbic acid eutectic composition with sorbic acid according to the mass ratio of 1:2 (dissolved with or without water). The preparation method is: heating a round-bottomed flask in a constant temperature water bath at 45° C., adjusting a rotor speed to 200-300 r/min, adding sorbic acid aqueous solution and Be into the round-bottomed flask, stirring and carrying out reaction for 12 h, and evaporating to remove water to synthesizing a Be/sorbic acid eutectic composition; or directly adding sorbic acid (dissolved without water) and Be into the round-bottomed flask, and stirring and carrying out reaction for 12 h to prepare the Be/sorbic acid eutectic composition.

(6) Be, as the HBA, is prepared into Be/cinnamic acid eutectic composition with cinnamic acid according to the mass ratio of 1:2 (dissolved with or without water). The preparation method is: heating a round-bottomed flask in a constant temperature water bath at 70° C., adjusting a rotor speed to 200-300 r/min, adding the aqueous solution of cinnamic acid and betaine into the round-bottomed flask, stirring and carrying out reaction for 12 h, and evaporating to remove water to synthesizing the Be/cinnamic acid eutectic composition; or directly adding cinnamic acid (dissolved without adding water) and Be into the round-bottomed flask, and stirring and carrying out reaction for 12 h to prepare the Be/cinnamic acid eutectic composition.

Table 3 shows the eutectic compositions prepared with Be as the HBA and different HBDs. Table 3 also shows whether the HBDs are dissolved in the solvent first and the mass ratio of raw materials.

TABLE 3

Characteristics of each eutectic composition in Comparative example 4

| Project | HBA | HBD | HBA solvent | HBD solvent | HBA:HBD | Homogeneous liquid | Dissolving EO | Dissolving in water |
|---|---|---|---|---|---|---|---|---|
| Comparative example 4 | Be | Ge | / | / | 1:1 | + | + | − |
| | | Ge | / | / | 1:2 | + | + | − |
| | | Ge | / | / | 1:3 | + | + | − |
| | | Gly | / | Ethylene glycol | 2:1 | + | + | − |
| | | Gly | / | Eethylene glycol | 4:1 | + | + | − |
| | | Gly | / | Ethylene glycol | 8:1 | + | + | − |
| | | Gly | / | Ethanol | 4:1 | − | / | / |
| | | Gly | / | Ethanol | 8:1 | − | / | / |
| | | Ga | / | Water | 1:2 | − | / | / |
| | | Ga | / | Ethanol and water | 1:2 | − | / | / |
| | | Ga | / | Ethylene glycol | 1:2 | + | − | − |
| | | Citric acid monohydrate | / | Water | 1:2 | + | − | + |
| | | Sorbic acid | / | / | 1:2 | − | / | / |
| | | Sorbic acid | / | Water | 1:2 | − | / | / |
| | | Cinnamic acid | / | / | 1:2 | − | / | / |
| | | Cinnamic acid | / | Water | 1:2 | − | / | / |

Table 3 also shows characteristics of each eutectic composition.

(1) BG-DES is a homogeneous liquid with good fluidity, has no special odor, may dissolve EO, but may not dissolve in water, and has poor effect on improving the greasy feeling of EO. If the product with EO as the main component and water as the main dispersion solvent is prepared, the greasy feeling of the BO composition may not be well improved.

(2) Be/glycyrrhizic acid eutectic composition: when ethylene glycol is added in the preparation process, the prepared eutectic composition is a homogeneous liquid with good fluidity, has no special odor, and may dissolve essential oil but not dissolve in water, and may not improve the greasy feeling of the EO composition well. When ethanol is added in the preparation process, the prepared eutectic composition is not homogeneous liquid, has poor fluidity, and may not dissolve essential oil and is insoluble in water.

(3) Be/gallic acid eutectic composition: when ethylene glycol is added in the preparation process, the prepared eutectic composition is a homogeneous liquid, but may not dissolve essential oil and is insoluble in water. When ethanol or mixed solvent of ethanol and water is added in the preparation process, the prepared eutectic composition is not homogeneous liquid.

(4) Be/citric acid monohydrate eutectic composition is a homogeneous liquid with good fluidity and may be dissolved in water, but may not dissolve essential oil and may not improve the greasy feeling of the EO composition.

(5) Be/sorbic acid eutectic composition is not heterogeneous liquid with poor fluidity, and may not promote the dissolution of essential oil in water.

(6) Be/cinnamic acid eutectic composition is not heterogeneous liquid with poor fluidity, and may not promote the dissolution of essential oil in water.

By comparing Embodiment 1 with Comparative examples 1-4, it may be seen that DES is the best delivery medium of essential oil, may be used to increase the solubility of essential oil in water, make the EO composition more stable and reduce the greasy feeling of essential oil. In addition, the eutectic composition has high safety.

In order to further illustrate the characteristics of DES, the technical effects of this eutectic composition are verified in combination with Embodiments 2-12.

Embodiment 2

Figure 3:
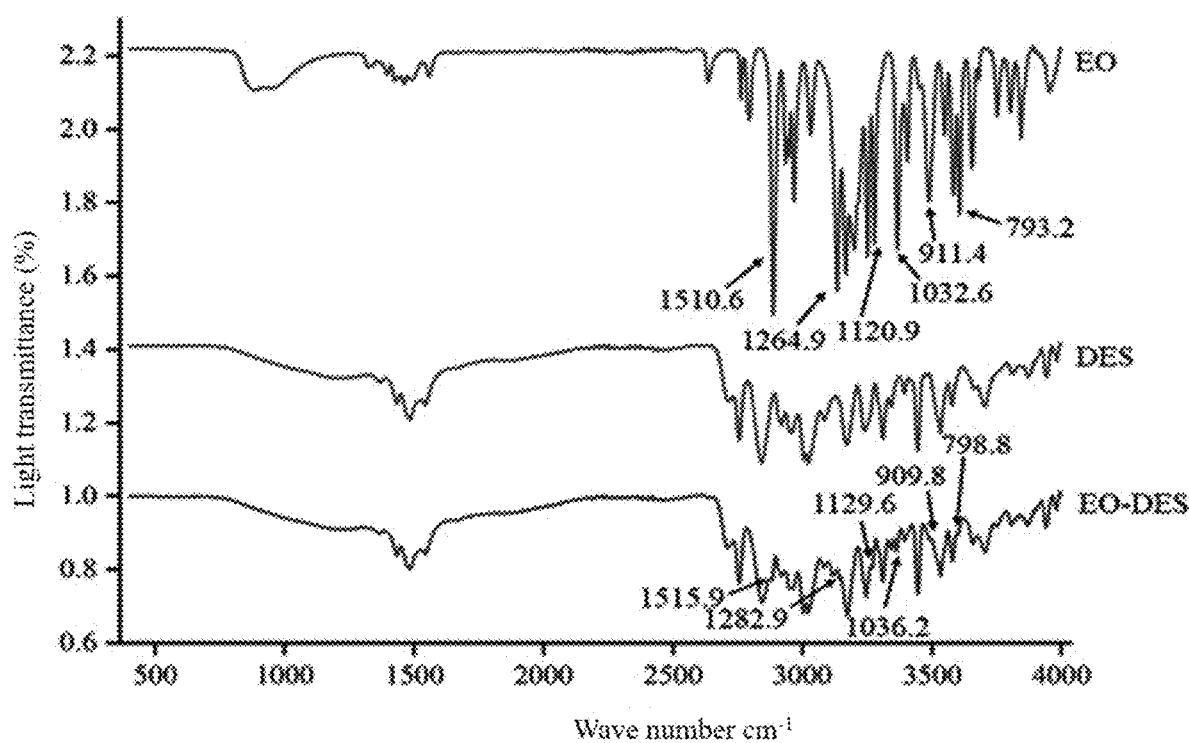
FIG. 3 shows infrared spectrums of EO, DES, and DES dissolving EO (EO-DES).

Referring to FIG. 3.

In order to verify the combination mode of DES with EO, three samples of the following preparations are analyzed using nuclear magnetic resonance hydrogen spectroscopy and infrared spectroscopy.

(1) 9 parts by mass of *Syringa oblata* Lindl. EO+91 parts by mass of DES (prepared by Ch and Ge in a mass ratio of 1:1); (2) 220 μL *Syringa oblata* Lindl. EO; (3) 220 μL of DES prepared by Ch and Ge according to the mass ratio of 1:1. The results are shown in FIG. 3.

NMR hydrogen spectrums of EO, DES and EO-DES (DES is dissolved with EO) are detected; the results show that when EO existed alone, EO has the hydrogen spectrum peak of phenolic hydroxyl group. When DES is dissolved with *Syringa oblata* Lindl. EO to obtain EO-DES, it was found that the hydrogen spectrum peak of phenolic hydroxyl group in EO disappeared.

FIG. 3 shows infrared spectrums of EO, DES and EO-DES from top to bottom. The infrared characteristic peaks of EO-DES have shifted to different degrees compared with the infrared characteristic peaks of EO alone, which shows that there is interaction between *Syringa oblata* Lindl. EO and DES in the process of dissolution, and the *Syringa oblata* Lindl. EO and DES are combined in the form of some covalent bond, not simply physical combination.

Therefore, from the infrared spectrums and NMR hydrogen spectrums, it may be seen that the combination of DES and EO provided by the disclosure is in the form of covalent bond, but not a simple dissolution process.

Embodiment 3

This embodiment is to determine the optimal water content in the EO composition. The optimal water content is that water may be evenly mixed with EO and DES without emulsification or stratification, and the fishy smell of Ch may be masked. Liquid preparations with *Syringa oblata* Lindl. EO content of 10%, 5% and 1% are prepared in the embodiment, and the eutectic composition used is prepared by Ch and Ge in a ratio of 1:2. The results are shown in Table 4.

TABLE 4

|  | EO | DES | H$_2$O |
|---|---|---|---|
| 10% | 10 | 27 | 63 |
| 5% | 5 | 28 | 67 |
| 1% | 1 | 30 | 69 |

As shown in Table 4, the highest ratio of water content in volatile oil delivery system namely EO-DES-W, containing 10% EO is EO:DES:W=10:27:63; the highest ratio of EO-DES-W containing 5% EO is EO:DES:W=5:28:67; the highest ratio of EO-DES-W containing 1% EO is EO:DES:W=1:30:69, and the proportion of water is about 60-70%. At this time, the delivery system may not only mask the fishy smell of Ch without emulsification or stratification, but also keep a heterogeneous, clear and transparent liquid. When the proportion of water is further increased, emulsification will occur and oil droplets will precipitate when standing.

Therefore, in the EO liquid preparation with water as dispersion solvent, namely EO-DES-W, when the content of essential oil is 1-10%, the water content is optimally controlled at 60-70%.

Embodiment 4

In order to verify the homogeneity and stability of the EO-DES-W delivery system formed by mixing the eutectic composition of the disclosure with water and essential oil, EO-DES-W delivery systems with 1%, 5% and 10% volatile oil are prepared according to the mass ratio of EO:DES:W=1:29:70, EO:DES:W=5:28:67 and EO:DES:W=10:27:63 respectively. DES is prepared by Ch and Ge in a ratio of 1:2.

Then, the polydispersity indexes (PDIs) of particle size in 1% EO-DES-W, 5% EO-DES-W and 10% EO-DES-W preparations are determined by a particle size potentiometer. The results are shown in Table 5. The PDIs of particle size in 1% EO-DES-W, 5% EO-DES-W and 10% EO-DES-W preparations are 0.28, 0.229 and 0.134, respectively, all less than 0.3.

TABLE 5

| EO-DES-W | 1% | 5% | 10% |
|---|---|---|---|
| PDI | 0.28 | 0.229 | 0.134 |

The above results show that the PDIs of the 1% EO-DES-W, 5% EO-DES-W and 10% EO-DES-W preparations are less than 0.3, and thus it is indicated that the EO-DES-W delivery system is transparent and heterogeneous. Therefore, DES provided in the disclosure may dissolve volatile oil and dissolve in water at the same time, and make the dispersion system of essential oil transparent and heterogeneous.

Embodiment 5

In order to verify the stability of DES combined with EO, three EO liquid preparations (1% EO-DES-W, 5% EO-DES-W and 10% EO-DES-W) in Embodiment 4 are centrifuged at 8000 rpm for 10 mins, and then the stratification situation is observed. At the same time, *Syringa oblata* Lindl. EO is mixed with water according to the mass ratio of 5:95 to obtain EO-W, and EO-W is centrifuged synchronously to observe stratification situation. The experimental results are shown in Table 6.

TABLE 6

| Preparation | PDI before centrifugation | PDI after centrifugation | Separation percentage (%) |
|---|---|---|---|
| EO-W | / | / | 100 |
| 1% EO-DES-W | 0.280 | 0.268 | 0 |
| 5% EO-DES-W | 0.221 | 0.229 | 0 |
| 10% EO-DES-W | 0.134 | 0.144 | 0 |

From the above experimental results, it may be seen that the three EO liquid preparations did not show any stratification or precipitation before and after centrifugation, and they are still homogeneous systems after centrifugation for 10 mins. However, the EO-W (produced by vortex mixing of EO and water) undergoes complete separation of oil and water after centrifugation. The PDI of the EO-DES-W delivery system formed by dissolving EO in DES and mixing with water has almost no change before and after centrifugation, and the essential oil is not separated from water. Therefore, it indicates that the EO-DES-W delivery system has good centrifugal stability.

Embodiment 6

Figure 4:
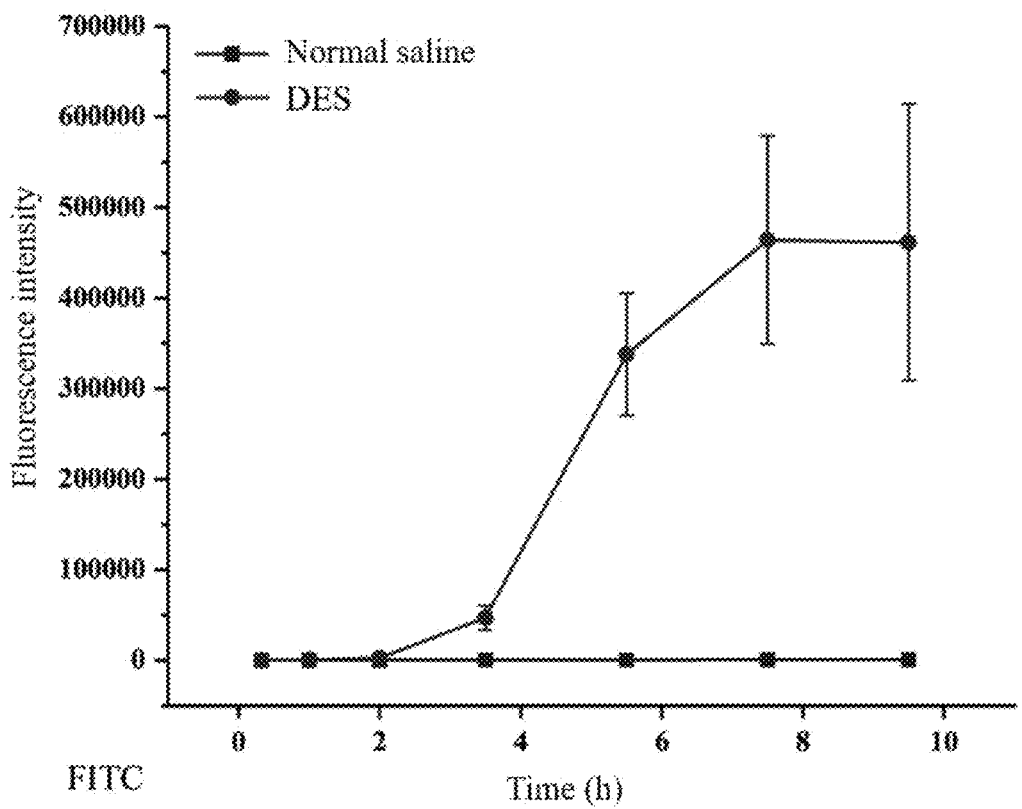
FIG. 4 shows experiment results of DES-fluorescein isothiocyanate isomer (FITC) and 1% Tween-80 normal saline-FITC in diffusion cell.
Figure 5:
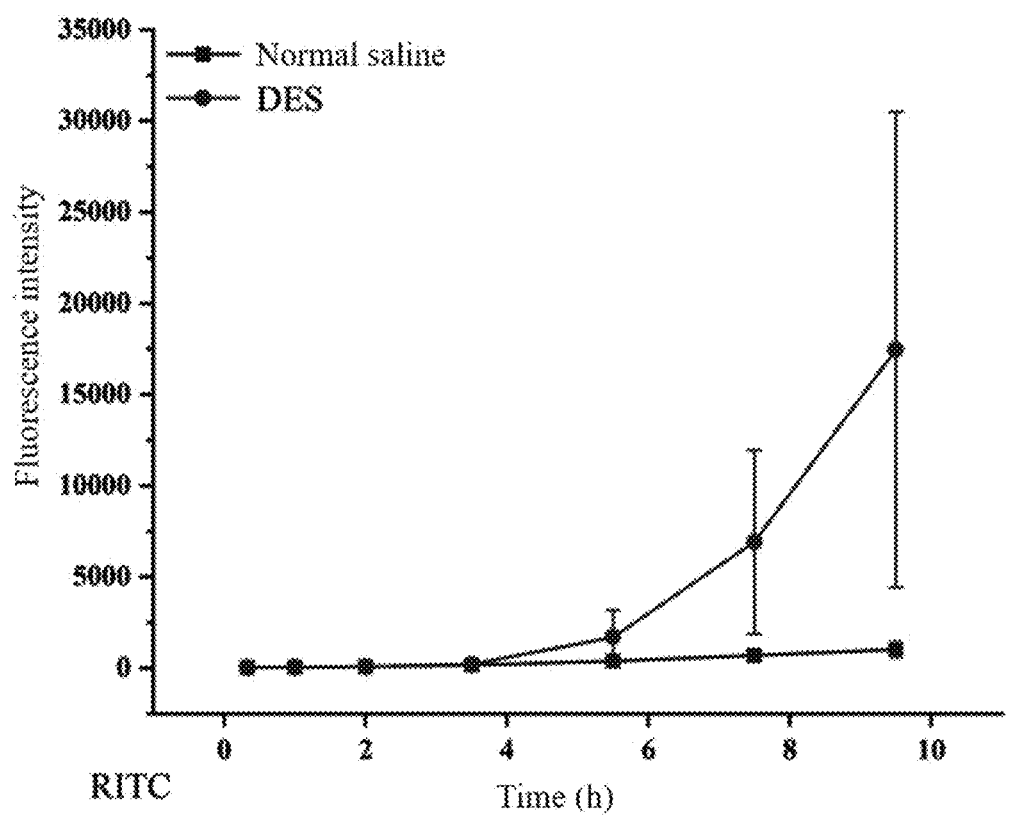
FIG. 5 shows experiment results of DES-rhodamine isothiocyanate (RITC) and 1% Tween-80 normal saline-RITC in diffusion cell.

Referring to FIG. 4 and FIG. 5.

This embodiment is to verify the skin permeability of DES (prepared by Ch and Ge in a mass ratio of 2:1). In order to detect the transdermal permeability of DES, the following diffusion cell experiments are carried out:
(1) dissolving 0.15 mg of fat-soluble fluorescent dye FITC in DES and 1% Tween-80 normal saline respectively for transdermal diffusion cell experiments.
(2) dissolving 0.15 mg of fat-soluble fluorescent dye RITC in DES and 1% Tween-80 normal saline respectively for transdermal diffusion cell experiments. The results are shown in FIG. 4 and FIG. 5.

As shown in FIG. 4, compared with 1% Tween-80 normal saline, DES has a significant advantage in the permeability of fat-soluble fluorescent dye FITC. As shown in FIG. 5, compared with 1% Tween-80 normal saline, DES has a significant advantage in the permeability of fat-soluble fluorescent dye RITC. According to the aforementioned experiments, compared with 1% Tween-80 normal saline, DES provided by the disclosure may open the stratum corneum of skin and significantly increase the transdermal permeability of fat-soluble substances, and has a strong penetration promoting effect.

Embodiment 7

Figure 6:
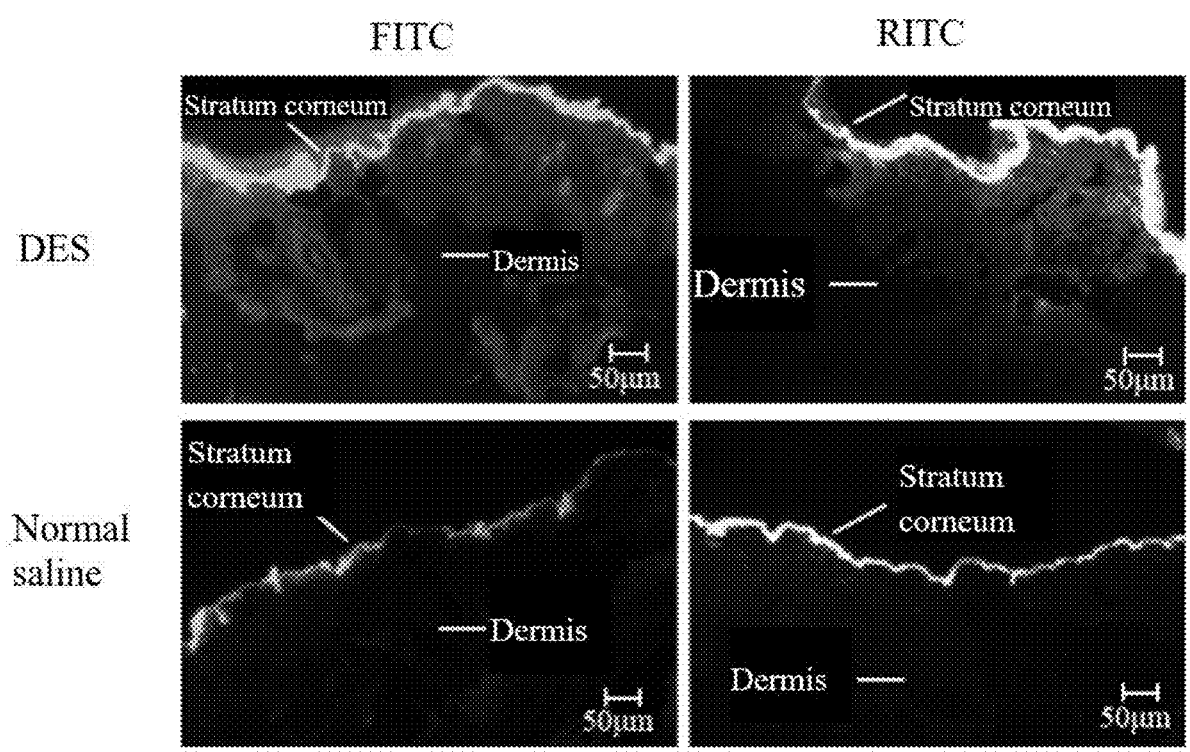
FIG. 6 shows in vivo permeation pictures (fluorescence intensity) of DES and 1% Tween-80 normal saline on different fluorescent dyes.
Figure 7:
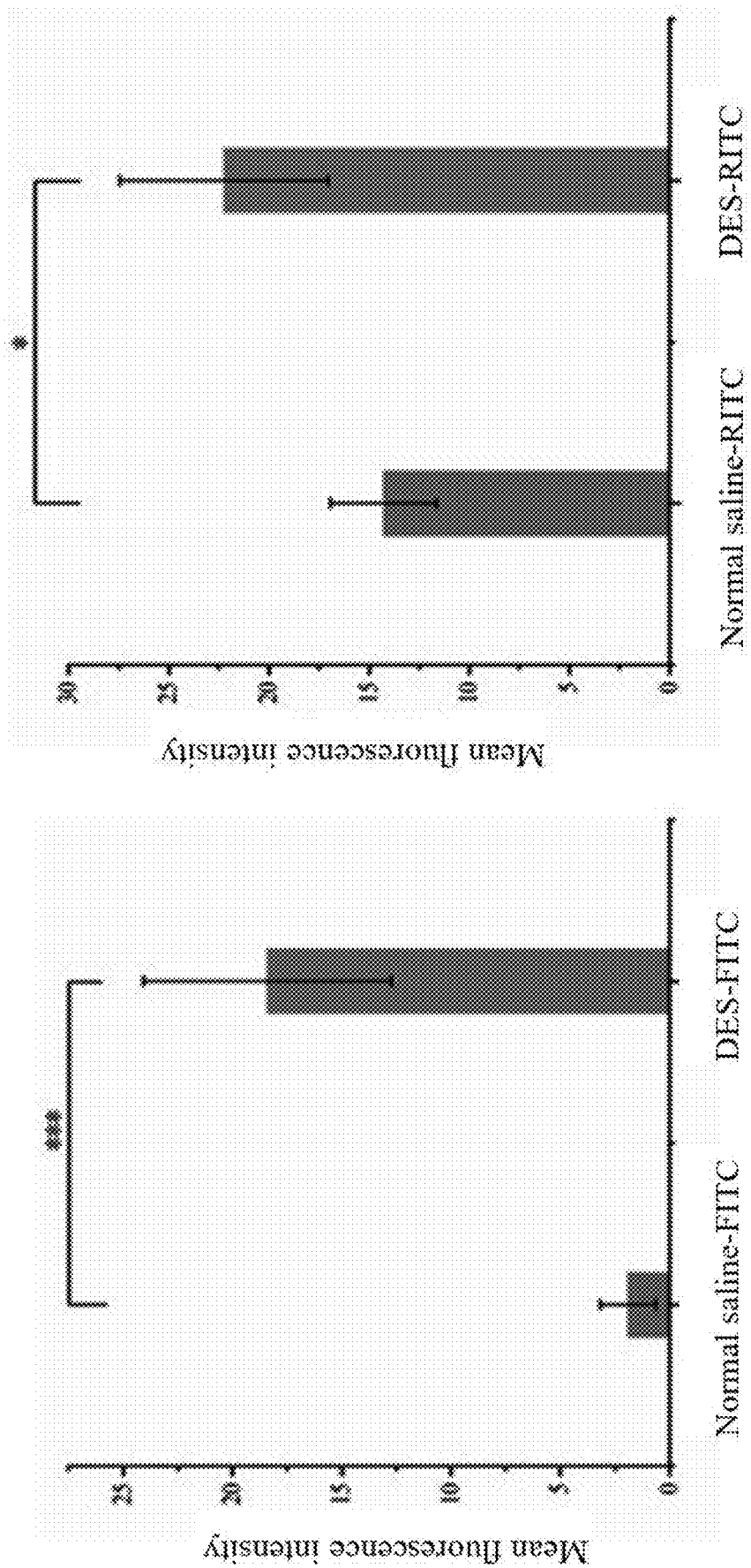
FIG. 7 shows semi-quantitative analysis diagram of fluorescence intensity of in vivo permeation pictures for different fluorescent dyes by using ImageJ software.

Referring to FIG. 6 and FIG. 7.

This embodiment is in vivo permeation tests of DES (prepared by Ch and Ge in a mass ratio of 2:1). In order to detect the permeability of DES in the skin of back of surviving mice, the following in vivo permeation tests are carried out:
(1) dissolving 0.15 mg of fat-soluble fluorescent dye FITC in DES and 1% Tween-80 normal saline respectively for the in vivo permeation test.
(2) dissolving 0.15 mg of fat-soluble fluorescent dye RITC in DES and 1% Tween-80 normal saline respectively for in vivo permeation test. The experimental results are shown in FIG. 6 and FIG. 7.

FIG. 7 shows semi-quantitative analysis of the in vivo permeation pictures of FIG. 6 by using ImageJ software. As may be seen from FIG. 6 and FIG. 7, the fluorescence intensity of DES group is significantly higher than that of 1% Tween-80 normal saline group (denoted as NaCl-FITC or NaCl-RITC), that is DES group is brighter; semi-quantitative analysis shows that DES-FITC is significantly higher than NaCl-FITC ($P<0.01$) and DES-RITC is higher than NaCl-RITC ($P<0.05$). Therefore, DES in the disclosure also has a strong penetration promoting effect on living mice.

Embodiment 8

Figure 8:
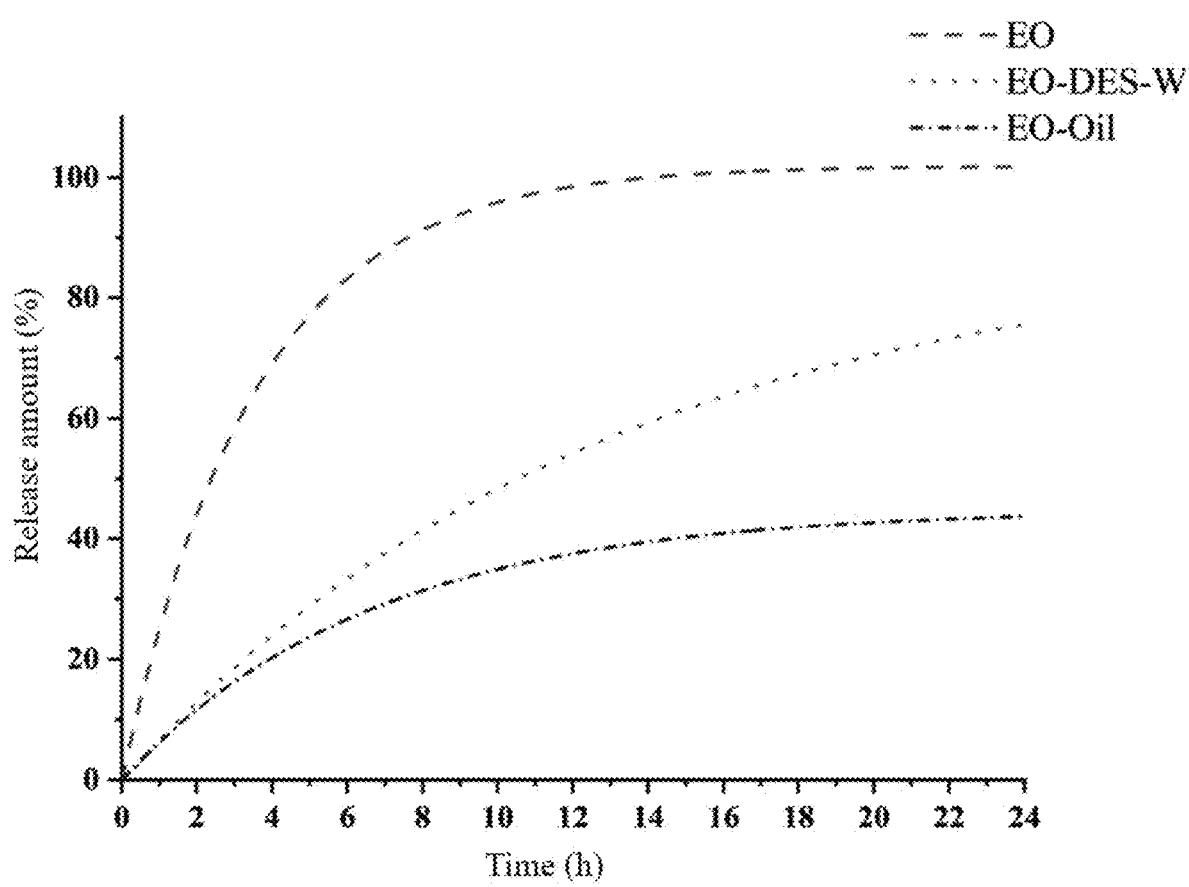
FIG. 8 shows in vitro release amount curves of EO, DES dissolving EO and dissolving in water (EO-DES-W) and EO dissolving in base oil (EO-Oil).

Referring to FIG. 8.

This embodiment is to verify the in vitro release of essential oil preparation made by DES (prepared by Ch and Ge in a mass ratio of 1:1). In order to detect the in vitro release of EO dissolved by DES, in vitro release tests are conducted to simulate the drug release in human epidermis. The following samples are prepared for the experiment:
(1) 10 μL pure *Chimonanthus nitens* Oliv. EO, marked as EO.
(2) EO liquid preparation, including 10 μL of *Chimonanthus nitens* Oliv. EO, 62 μL of DES and 128 μL of water, marked as EO-DES-W.
(3) dissolving 10 μL of *Chimonanthus nitens* Oliv. EO in 190 μL of base oil (non-volatile oil), marked as EO-Oil.

The temperature of the incubator is set to the body surface temperature of 32° C., and the above three preparations (EO, EO-DES-W and EO-Oil) are taken and put in the incubator with open opening, respectively. Samples are taken for detecting at 0 h, 0.5 h, 1 h, 2 h, 3 h, 5 h, 7 h, 9 h, 11 h and 24 h. The contents of *Chimonanthus nitens* Oliv. EO in three preparations are determined by gas chromatography-mass spectrometry with eudesmol, the main component in the *Chimonanthus nitens* Oliv. EO, as a marker. The experimental results are shown in FIG. 8.

As may be seen from FIG. 8, in the in vitro release of the above three preparations, EO is completely released at 9 h, and EO-DES-W and EO-Oil are released at 24 h, respectively, and their release curves are in line with the general characteristics of drug release curves in vitro. It is proved that the in vitro release effect of EO liquid preparation composed of EO, DES and water meets the requirements.

Embodiment 9

Figure 9:
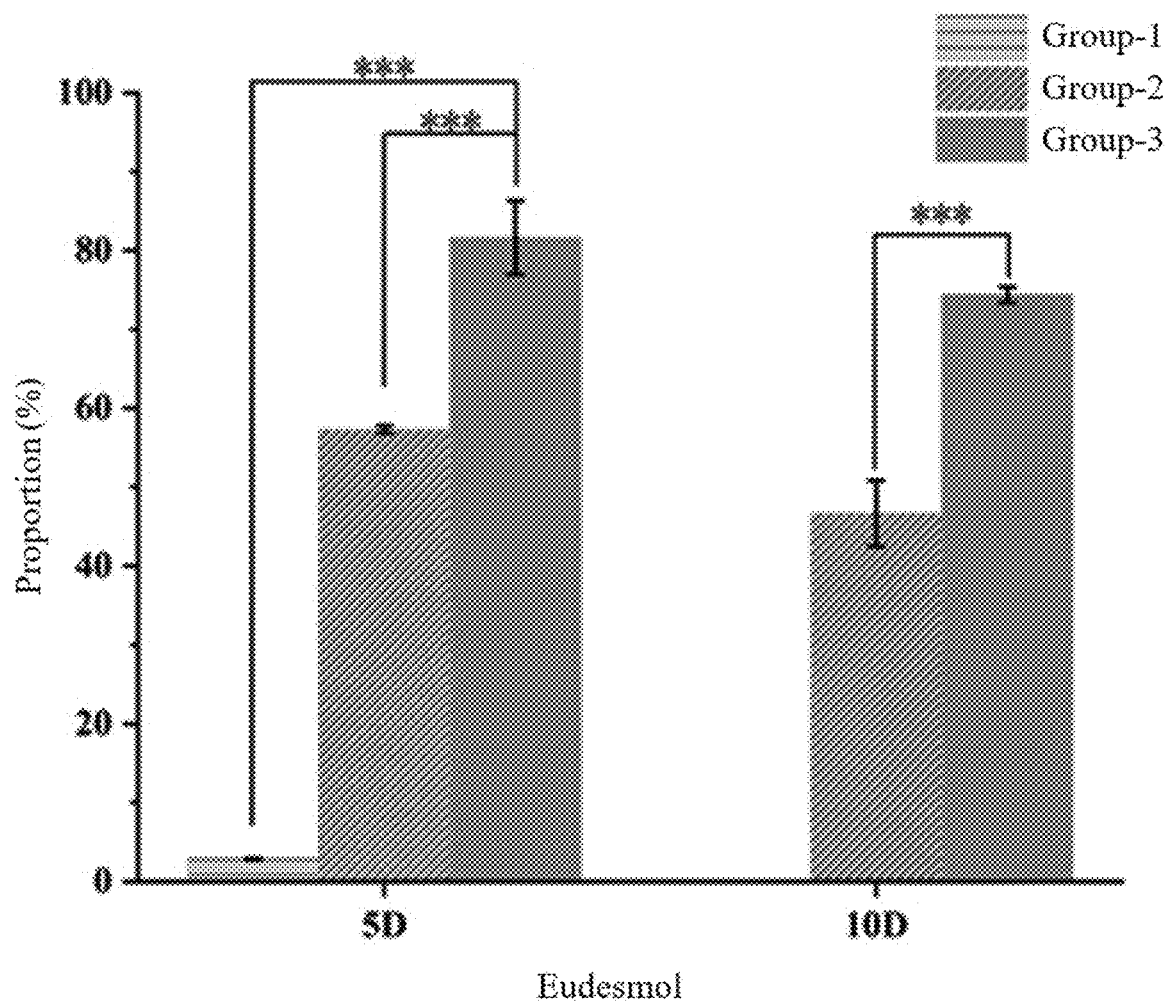
FIG. 9 shows results of determination of high temperature stability of pure *Chimonanthus nitens* Oliv. EO, EO-DES-W and traditional EO-Oil system with eudesmol in *Chimonanthus nitens* Oliv. EO as a marker.
Figure 10:
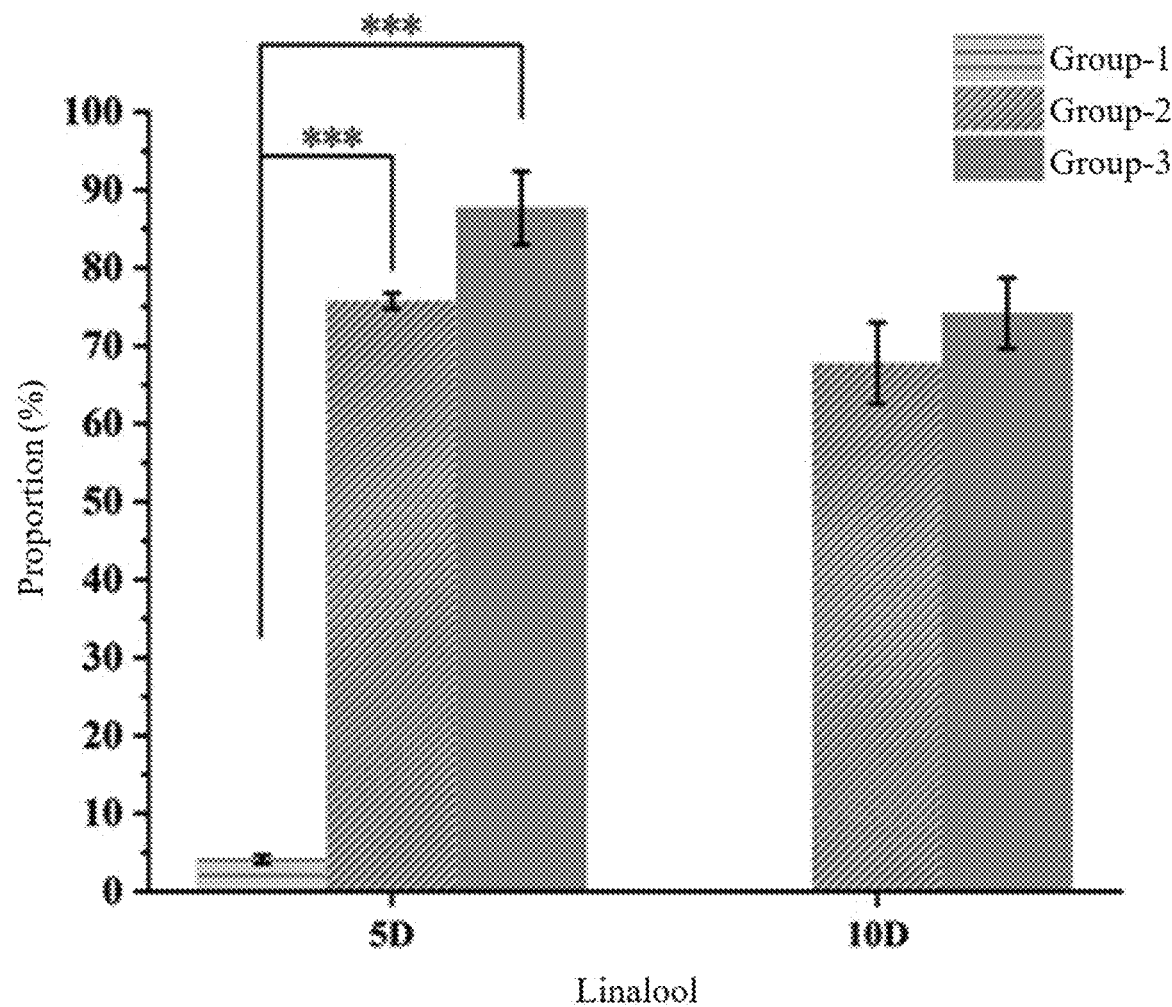
FIG. 10 shows results of determination of high temperature stability of pure *Chimonanthus nitens* Oliv. EO, EO-DES-W and traditional EO-Oil system with linalool in *Chimonanthus nitens* Oliv. EO as a marker.

Referring to FIG. 9 and FIG. 10.

This embodiment is to verify the high temperature stability of EO liquid preparation made by DES. In order to detect the high-temperature stability of DES (prepared by Ch and Ge in a ratio of 1:2) after dissolving EO, the following high-temperature stability experiment are carried out. The following samples are prepared for the experiment:
(1) 10 μL pure *Chimonanthus nitens* Oliv. EO, marked as Group-1.
(2) EO liquid preparation, namely EO-DES-W, including 10 μL of *Chimonanthus nitens* Oliv. EO, 62 μL of DES and 128 μL of water, marked as Group-2.
(3) traditional base oil-essential oil system, including 10 μL of *Chimonanthus nitens* Oliv. EO dissolved in 190 μL of base oil (non-volatile oil), marked as Group-3.

The above-mentioned samples are placed in the environment of 40° C., and taken out on the 5th and 10th day respectively. The contents of the *Chimonanthus nitens* Oliv. EO in the three preparations are detected by gas chromatography-mass spectrometry with eudesmol and linalool, the main component in the *Chimonanthus nitens* Oliv. EO, as markers. The experimental results are shown in FIG. 9 and FIG. 10.

It may be seen from FIG. 9 that when eudesmol, the main component of *Chimonanthus nitens* Oliv. EO, is used as a marker, the contents of the *Chimonanthus nitens* Oliv. EO in Group-2 and Group-3 are higher than that of Group-1. It may be seen from FIG. 10 that when linalool, the main component of *Chimonanthus praecox* EO, is used as a marker, the contents of the *Chimonanthus nitens* Oliv. EO in Group-2 and Group-3 are higher than that in Group-1, and there is no significant difference between Group-2 and Group-3. However, as a large amount of base oil is used in Group-3, the Group-3 has strong greasy feeling and poor skin friendliness of essential oil preparation.

The above experiments prove that DES provided by the disclosure has good high-temperature stability for EO, and thus makes the essential oil preparation less volatile when stored at ambient temperature.

Embodiment 10

Figure 11:
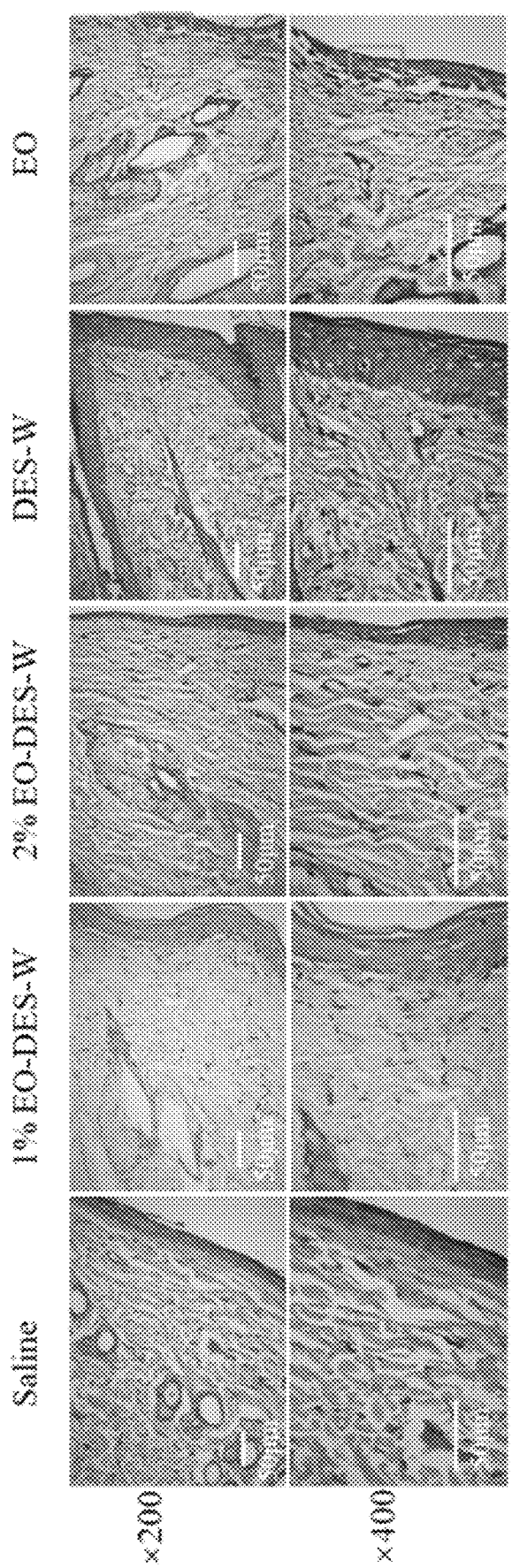
FIG. 11 shows Massion and hematoxylin-eosin (H&E) staining pictures for skin irritation of samples: normal saline, 1% EO-DES-W, 2% EO-DES-W, blank substrate (DES and water, DES-W) and pure EO.

Referring to FIG. 11.

This embodiment is to verify the skin irritation of EO liquid preparation made by DES. In order to prove the safety of EO liquid preparation, irritation to skin and whether it may reach the corresponding safety index, the skin irritation experiment is carried out. The following samples are prepared for the experiment:
(1) Normal Saline: 200 μL normal saline, marked as Saline.
(2) EO liquid preparation containing 1% EO: including 8 μL of *Camellia sinensis* EO, 240 μL of DES and 552 μL of water, marked as 1% EO-DES-W.
(3) EO liquid preparation containing 2% EO: including 16 μL of *Camellia sinensis* EO, 256 μL of DES and 528 μL of water, marked as 2% EO-DES-W.
(4) Blank substrate control group: including 216 μL DES and 584 μL water, marked as DES-W.
(5) pure essential oil group: 800 μL of essential oil, marked as EO.

The above five groups of samples are taken and smeared about 150 μL on each mouse's skin of back (three parallel experiments are conducted for each preparation), and the hair is cut off with a razor with an area of 2×2 cm. The samples are applied evenly once a day for five days. At the end of the fifth day, the mice are killed, and the skin tissue in the experimental area is cut off, washed with distilled water, fixed with 4% paraformaldehyde, embedded in paraffin, stained with H&E and observed under microscope. The experimental results are shown in FIG. 11.

As shown in FIG. 11, the epidermal cells in Saline, 1% EO-DES-W, 2% EO-DES-W and DES-W groups are not damaged, but the epidermal cells in EO group are damaged or missing. It shows that Saline, 1% EO-DES-W, 2% EO-DES-W and DES-W groups have good safety.

Embodiment 11

Figure 12:
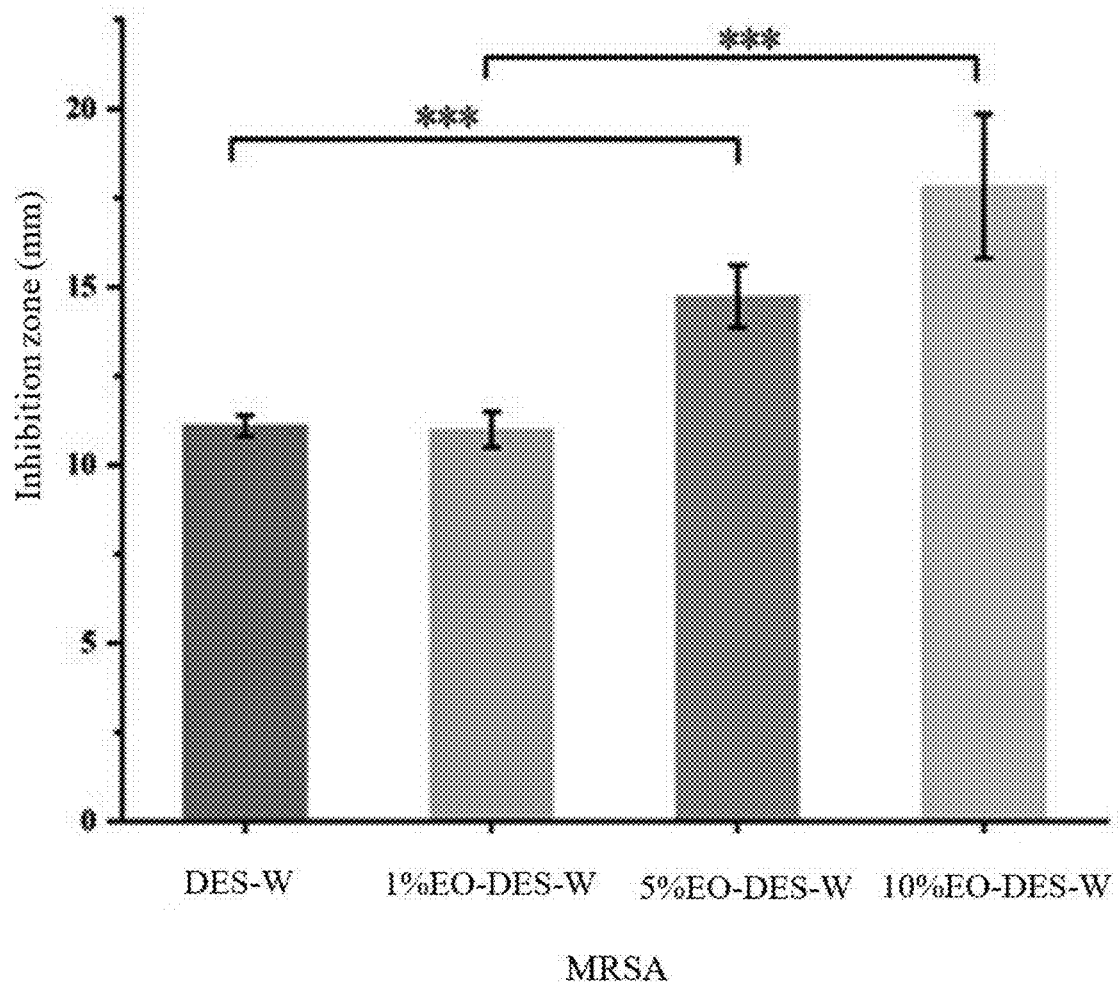
FIG. 12 shows in vitro antibacterial effects of DES-W, 1% EO-DES-W, 5% EO-DES-W and 10% EO-DES-W on methicillin-resistant *Staphylococcus aureus* (MRSA).
Figure 13:
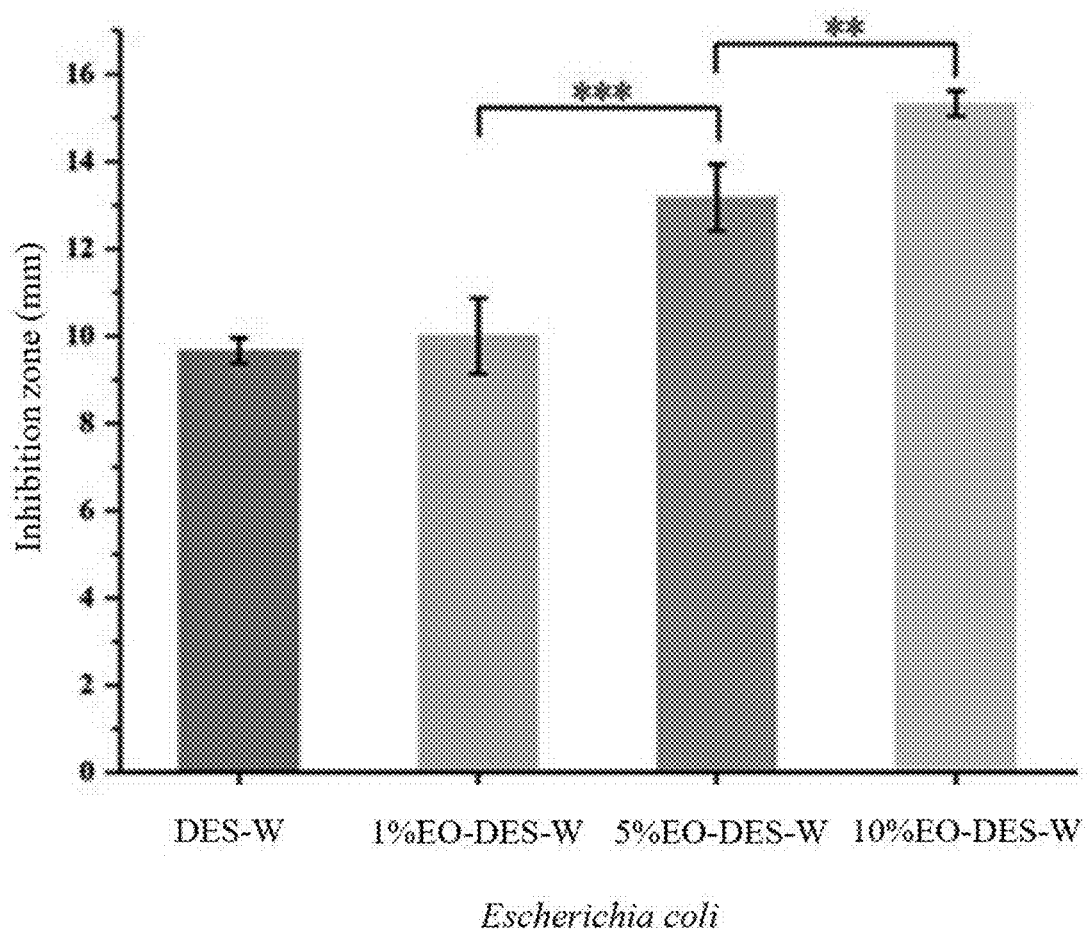
FIG. 13 shows in vitro antibacterial effects of DES-W, 1% EO-DES-W, 5% EO-DES-W and 10% EO-DES-W on *Escherichia coli*.

Referring to FIG. 12 and FIG. 13.

This embodiment is to verify the in vitro antibacterial ability of EO liquid preparation made by DES (prepared by Ch and Ge in a ratio of 1:2). In order to prove the antibacterial effect of EO liquid preparation, the size of inhibition zone against common strains is tested to prove the antibacterial performance of EO liquid preparation. The EO in this experiment is *Syringa oblata* Lindl. EO, and *Syringa oblata* Lindl. EO is an antibacterial drug, and may significantly inhibit the growth and reproduction of bacteria and fungi. The following samples are prepared for the experiment:

(1) Blank substrate: mixed system of pure substrate and water, including 30 μL DES and 70 μL water, marked as DES-W.
(2) EO liquid preparation containing 1% EO, including 1 μL *Syringa oblata* Lindl. EO, 29 μL DES and 70 μL water, marked as 1% EO-DES-W.
(3) EO liquid preparation containing 5% EO, including 5 μL *Syringa oblata* Lindl. EO, 25 μL DES and 70 μL water, marked as 5% EO-DES-W.
(4) EO liquid preparation containing 10% EO, including 10 μL *Syringa oblata* Lindl. EO, 27 μL DES and 63 μL water, marked as 10% EO-DES-W.

In this embodiment, MRSA and *Escherichia coli* are used as antibacterial test objects. MRSA is the representative bacteria of Gram-positive bacteria and *Escherichia coli* is the representative bacteria of Gram-negative bacteria. The experimental method is as follows:

100 μL of bacterial liquid in logarithmic growth phase is coated in a Petri dish containing LB medium, and the Petri dish is perforated with a diameter of 6 mm, and then the corresponding samples to be tested are dropped into the holes. Next, the culture medium is place in a closed environment at 37° C. for about 4 h, and then inverted for 18 h. Then, the size of inhibition zone is observed. The experimental results are shown in FIG. 12 and FIG. 13.

For MRSA and *Escherichia coli*, 10% EO-DES-W has the strongest antibacterial effect, and the size of the inhibition zone is about 17-18 mm, which shows that it has sensitive antibacterial effect on both strains. The size of the inhibition zone of 5% EO-DES-W is about 14 mm, and its antibacterial effect is slightly weaker than that of 10% EO-DES-W. Compared with DES-W and 1% EO-DES-W, 5% EO-DES-W have significant differences in antibacterial effects.

The above experiments prove that the EO-DES-W has sensitive antibacterial effect and obvious in vitro antibacterial effect, among which DES is made of Ch and Ge and has weak antibacterial effect, and *Syringa oblata* Lindl. EO plays the main antibacterial effect.

Embodiment 12

Referring to FIG. 14 to FIG. 18.

This embodiment is to verify the in vivo antibacterial ability of EO liquid preparation made by DES (prepared by Ch and Ge in a ratio of 1:1). In order to verify whether the EO liquid preparation has good antibacterial effect and safety in vivo, Balc mice are used to establish a wound infection model and observe the therapeutic effect of the EO liquid preparation. The experiment is divided into four groups, namely:
Group 1: PBS group;
Group 2: blank substrate: mixed system of pure DES and water, including 30 μL DES and 70 μL W, marked as DES-W.
Group 3: EO liquid preparation containing 1% EO, including 1 μL *Syringa oblata* Lindl. EO, 29 μL DES and 70 μL water, marked as 1% EO-DES-W.
Group 4: EO liquid preparation containing 5% EO, including 5 μL *Syringa oblata* Lindl. EO, 25 μL DES, 70 μL W, marked as 5% EO-DES-W.

Sixteen Balc mice (divided into 4 groups with 4 mice in each group) of about 17 g are fed for one week. The day before the experiment, the hair on the back of mice is shaved with depilatory cream and clipper. On the day of the experiment, a round wound with a diameter of about 5-6 mm is cut out on the back of mice with surgical scissors, and 10 μL of MRSA in the logarithmic growth phase is added to bind the wound. The next day, the wound suppurates, the mold is successful. The mice are weighed every day and taken photos of the wound; the wounds of four groups of mice are treated with 10 μL of the four groups of preparations, twice a day, and repeated for 3 days. After 3 days, the bacteria in the wounds of mice are dipped in the plate counting agar for surface culture. Next, the culture plate is cultured at 37° C. for 24 h and then the bacteria are counted to observe the trend. After 12 days, the mice are killed, and the skin, heart, spleen, lung and kidney of the mice are taken for Massion and H&E staining sections.

Figure 14:
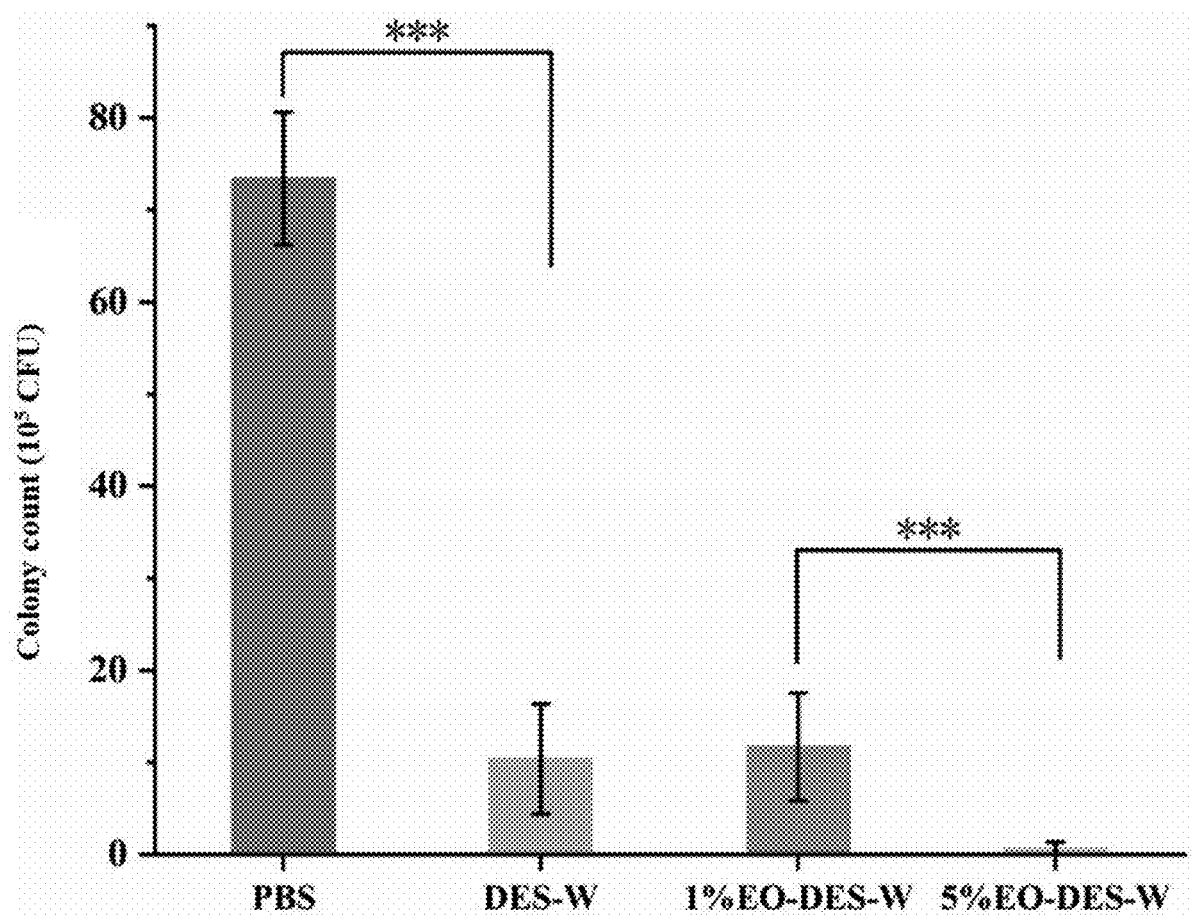
FIG. 14 shows in vivo antibacterial effects of phosphate-buffered saline (PBS), DES-W, 1% EO-DES-W and 5% EO-DES-W, with MRSA as the test object.
Figure 15:
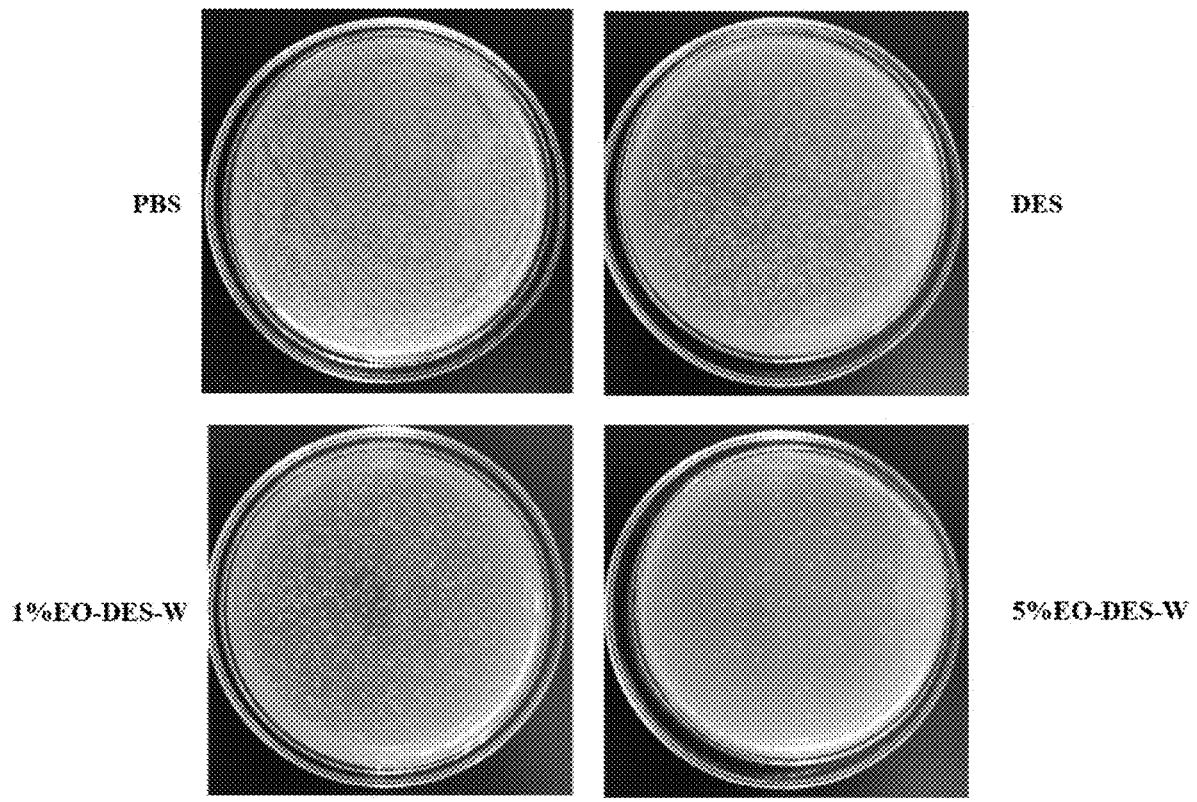
FIG. 15 shows in vivo antibacterial effects of PBS, DES-W, 1% EO-DES-W and 5% EO-DES-W, with *Escherichia coli* as the test object.

The results are shown in FIG. 14 and FIG. 15: the number of colonies in PBS group is significantly larger than that in the other three groups, with the most bacterial infections; the number of colonies in DES group is similar to that in 1% EO-DES-W group, there is no significant difference, and thus it indicates that the content of essential oil is too low and the in vivo antibacterial effect is poor. 5% EO-DES-W group has the least bacteria, and thereby it indicates that 5% EO-DES-W has the best antibacterial effect compared with other groups. Pure DES and 1% EO-DES-W also have certain antibacterial effects on the back of mice.

Figure 16A:
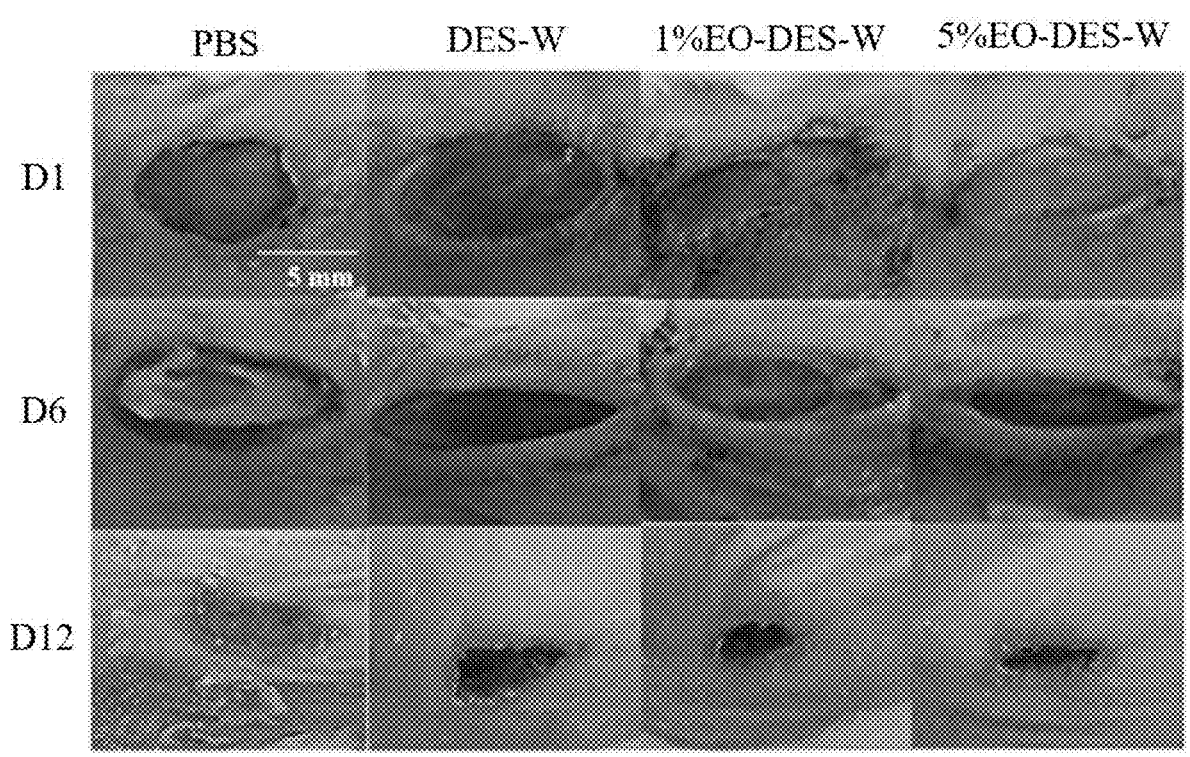
FIG. 16A is a picture of wound healing in mice, and shows wound healing situation of model mice after treatment with PBS, DES-W, 1% EO-DES-W and 5% EO-DES-W.
Figure 16B:
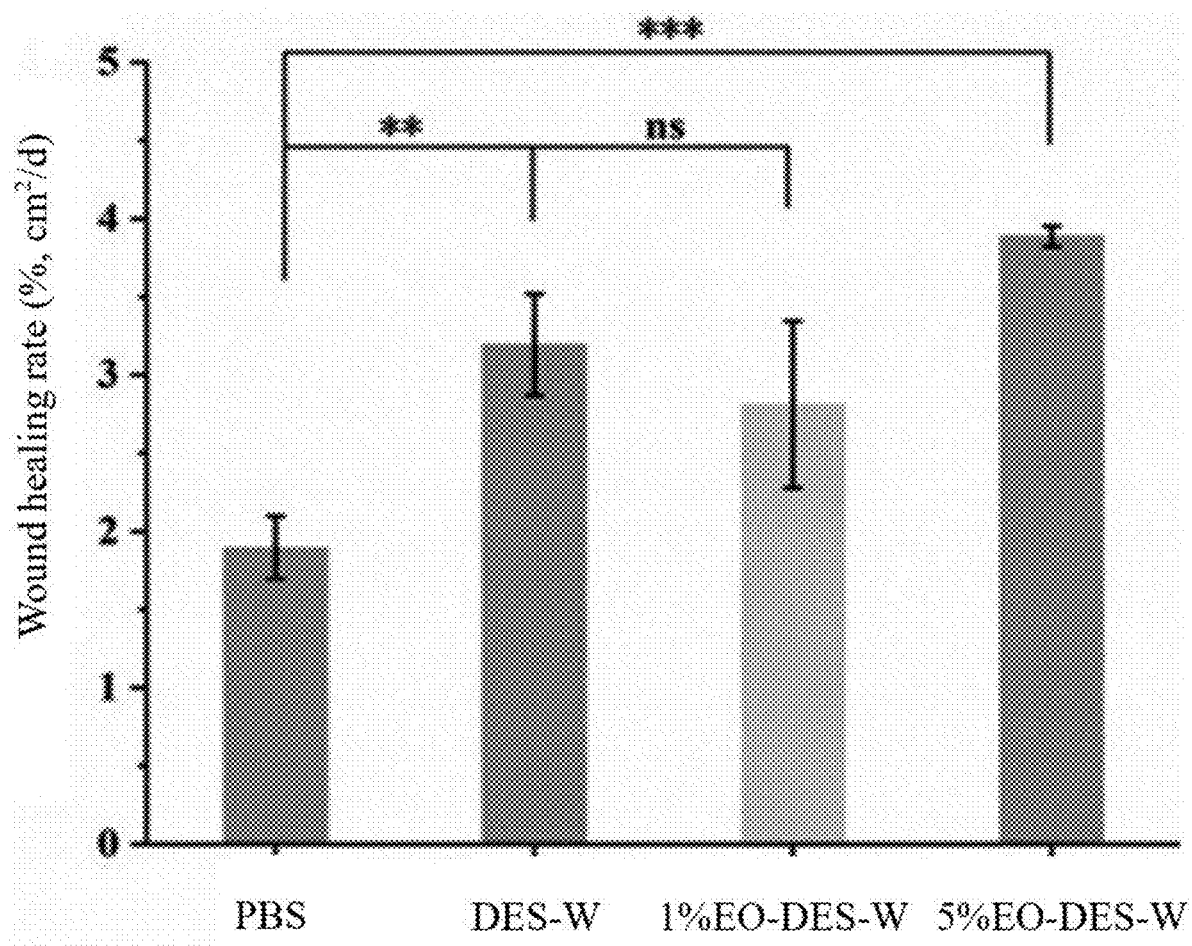
FIG. 16B is a statistical graph of wound healing rate in mice, and shows wound healing situation of model mice after treatment with PBS, DES-W, 1% EO-DES-W and 5% EO-DES-W.

Referring to FIG. 16A and FIG. 16B, FIG. 16A is a picture of wound healing in mice, and FIG. 16B is a statistical graph of wound healing rate in mice. As may be seen from the FIG. 16A and FIG. 16B, the rate of wound healing area (healing area/original mouth area×100%) in PBS group is the smallest and the healing velocity is the slowest; the area rate of wound healing in DES and 1% EO-DES-W group is larger than that in PBS group and healing velocity is faster ($P<0.05$), and the velocity of wound healing in 5% EO-DES-W group is the fastest, and the area rate of wound healing is more significant than that in DES and 1% EO-DES-W group and PBS group ($P<0.01$).

Figure 17:
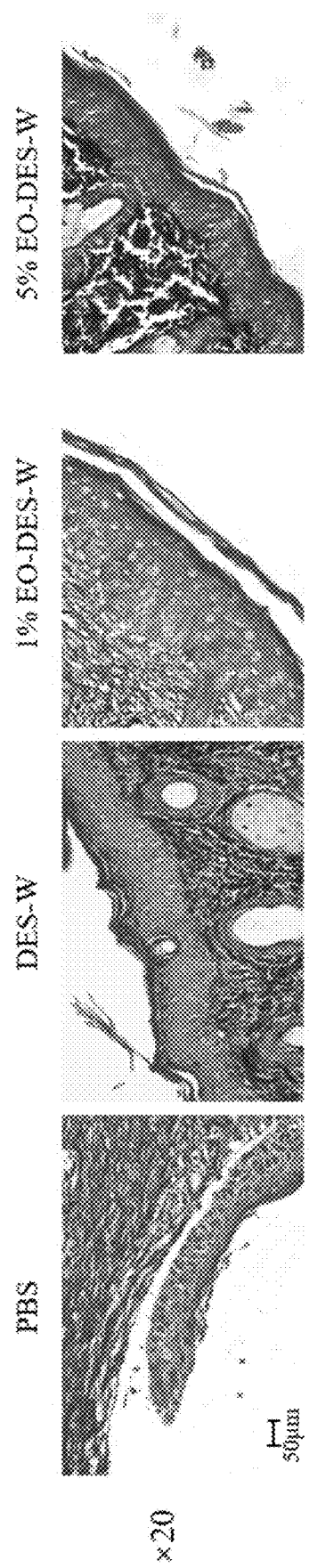
FIG. 17 shows Massion sections of the wound site of model mice after treatment with PBS, DES-W, 1% EO-DES-W and 5% EO-DES-W.

The Massion sections in FIG. 17 show that the skin of PBS group is damaged and there are no hair follicle cells; hair follicle cells appeared in DES-W group, and collagen deposition in dermis was obvious. Collagen deposition in epidermis of 1% EO-DES-W group means that epidermis begins to recover gradually. In 5% EO-DES-W group, epidermal collagen decreased, sebaceous glands in hair follicles recovered, acanthocytes arranged compactly, and epidermis recovered.

Figure 18:
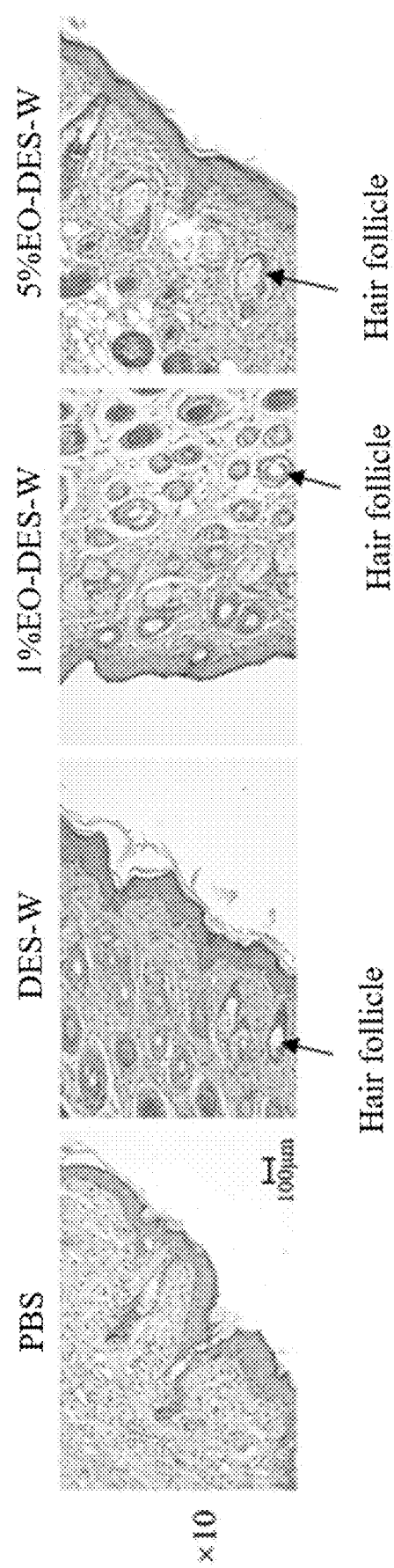
FIG. 18 shows H&E sections of the skin of model mice after treatment with PBS, DES-W, 1% EO-DES-W and 5% EO-DES-W.

The H&E sections in FIG. 18 show that the surface layer of skin in PBS group is seriously damaged and inflammatory cells are obviously aggregated; DES-W hair follicles begin to appear in large numbers, and the epidermis is not damaged; in 1% EO-DES-W group, the granulation tissue of dermis begins to appear obviously. In 5% EO-DES-W group, the sebaceous glands in hair follicles are normal in shape and the skin surface is smooth and compact.

Finally, it should be explained that the above embodiments are only used to illustrate the technical scheme of the disclosure, but not to limit it; although the present disclosure has been described in detail with reference to the foregoing embodiments, it should be understood by those skilled in the art that the technical scheme described in the foregoing embodiments may still be modified, or some or all of its technical features may be replaced by equivalents; however, these modifications or substitutions do not make the essence of the corresponding technical solutions deviate from the scope of the technical solutions of various embodiments of the disclosure.

What is claimed is:

1. An essential oil composition, comprising a eutectic composition and an essential oil; the eutectic composition comprises a hydrogen-bond donor and a hydrogen-bond acceptor;

the hydrogen-bond acceptor is 1-2 parts by mass of choline, and the hydrogen-bond donor is 1-2 parts by mass of geranic acid; a preparation method of the eutectic composition comprises: mixing the choline and the geranic acid in a reactor, heating to less than or equal to 45° C. for dissolution, stirring and carrying out reaction for more than 2 h to obtain a product, evaporating water in the product at less than or equal to 60° C., and then drying the product at less than or equal to 60° C. to obtain a choline/geranic acid eutectic composition;

the essential oil composition is an essential oil liquid preparation with water as a dispersion solvent, wherein an essential oil content is 1-10% and a water content is 60-70%;

wherein the essential oil is a volatile oil extracted from *Syringa oblata* Lindl.

2. The essential oil composition according to claim 1, wherein the essential oil is extracted from roots, stems, leaves or fruits of plants; an extraction method of the essential oil is any one or more of steam distillation, squeezing, organic solvent extraction and supercritical fluid extraction.

3. The essential oil composition according to claim 1, wherein the essential oil composition is a disinfectant for external use, a transdermal preparation or an oral preparation.

4. A preparation method of the essential oil composition according to claim 1, comprising: stirring or ultrasonically mixing the eutectic composition with the essential oil, and diluting to a predetermined concentration by adding water, so as to obtain the essential oil composition; the essential oil composition is the essential oil liquid preparation; the water is any one or more of tap water, distilled water, de-ionized water and ultrapure water.

* * * * *